(12) United States Patent
Finke et al.

(10) Patent No.: US 8,852,565 B2
(45) Date of Patent: Oct. 7, 2014

(54) ODOUR-REDUCING SUBSTANCES

(75) Inventors: Anja Finke, Holzminden (DE); Erich Dilk, Holzminden (DE)

(73) Assignee: Symrise AG, Holzminden (DE)

( * ) Notice: Subject to any disclaimer, the term of this patent is extended or adjusted under 35 U.S.C. 154(b) by 1043 days.

(21) Appl. No.: 12/405,730

(22) Filed: Mar. 17, 2009

(65) Prior Publication Data

US 2009/0238787 A1    Sep. 24, 2009

(30) Foreign Application Priority Data

Mar. 19, 2008   (EP) .................................. 08153042

(51) Int. Cl.
| | | |
|---|---|---|
| *A61K 8/37* | (2006.01) | |
| *A61L 11/00* | (2006.01) | |
| *A61L 9/01* | (2006.01) | |
| *A61Q 13/00* | (2006.01) | |
| *A61Q 15/00* | (2006.01) | |
| *A61K 8/34* | (2006.01) | |
| *D06M 23/12* | (2006.01) | |
| *C11B 9/00* | (2006.01) | |
| *D06M 23/06* | (2006.01) | |
| *A61Q 90/00* | (2009.01) | |
| *D06M 13/00* | (2006.01) | |

(52) U.S. Cl.
CPC ................. *A61L 9/01* (2013.01); *D06M 23/12* (2013.01); *C11B 9/0019* (2013.01); *D06M 23/06* (2013.01); *A61Q 90/00* (2013.01); *A61K 8/34* (2013.01); *A61Q 13/00* (2013.01); *A61K 8/375* (2013.01); *D06M 13/005* (2013.01)
USPC ........... 424/65; 424/76.6; 424/76.1; 510/107; 512/26

(58) Field of Classification Search
None
See application file for complete search history.

(56) References Cited

U.S. PATENT DOCUMENTS

| | | | |
|---|---|---|---|
| 3,091,632 A | | 5/1963 | Hagemeyer et al. |
| 3,329,713 A | | 7/1967 | Hoyle et al. |
| 3,408,388 A | | 10/1968 | Hagemeyer et al. |
| 4,091,090 A | | 5/1978 | Sipos |
| 4,498,996 A | | 2/1985 | Klemarczyk |
| 5,166,413 A | | 11/1992 | Ankner et al. |
| 5,500,154 A | * | 3/1996 | Bacon et al. .................. 510/102 |
| 5,538,719 A | | 7/1996 | Preti et al. |
| 5,559,271 A | | 9/1996 | Shaw et al. |
| 5,942,467 A | | 8/1999 | Rayborn, Sr. et al. |
| 6,372,201 B1 | * | 4/2002 | Leuridan et al. ................ 424/61 |
| 7,157,411 B2 | | 1/2007 | Rohde et al. |
| 2003/0228996 A1 | * | 12/2003 | Hei et al. ....................... 510/382 |
| 2009/0092576 A1 | * | 4/2009 | Trimble ..................... 424/78.07 |

FOREIGN PATENT DOCUMENTS

| | | | |
|---|---|---|---|
| DE | 3403696 | 8/1985 | |
| DE | 10207747 | 9/2002 | |
| EP | 0390539 | * 10/1990 | ............. A01N 43/78 |
| EP | 0780132 | 6/1997 | |
| EP | 799174 | 10/1997 | |
| EP | 1113105 | 7/2001 | |
| EP | 1269983 | 1/2003 | |
| EP | 1447102 | 8/2004 | |
| FR | 2867972 | 9/2005 | |
| JP | 1056798 | 3/1989 | |
| JP | 11222574 | 8/1999 | |
| JP | 2003113392 | 4/2003 | |
| JP | 2003171635 | 6/2003 | |
| JP | 2004035564 A | 2/2004 | |
| WO | WO-9521606 | 8/1995 | |
| WO | WO-9824752 | 6/1998 | |
| WO | WO-9827261 | 6/1998 | |
| WO | WO-0143784 | 6/2001 | |
| WO | WO-0241861 | 5/2002 | |
| WO | WO-03024907 | 3/2003 | |
| WO | WO-2004062363 | 7/2004 | |
| WO | WO-2005004601 | 1/2005 | |

OTHER PUBLICATIONS

Rowe, D. J., Chemistry and Technology of Flavours and Fragrances, 2005, Blackwell publishing, p. 63.*
Food Res. Int. 2001, 34, 473-481.
J. Food Science 2002, 67, 848-854.
Liebigs Ann. 1972, 756, 162-169.
Nippon Nogei Kagaku Kaishi (1968), 62(12), pp. 1763-1768.
Nippon Nogei Kagaku Kaishi (1989), 63(7), pp. 1231-1234.
Yukagaku (1989), 38(9), pp. 689-693.
Yukagaku (1993), 42(1), pp. 44-48.
First Office Action from the Japanese Patent Office issued in parallel Japanese Application No. 2009-097432 together with the English summary.

* cited by examiner

*Primary Examiner* — Mina Haghighatian
*Assistant Examiner* — Erin Hirt
(74) *Attorney, Agent, or Firm* — Dilworth & Barrese, LLP

(57) ABSTRACT

The use is described
(i)(a) of a single alcohol of formula (1) or
(i)(b) of a mixture comprising or consisting of two or more different alcohols of formula (1), (1)

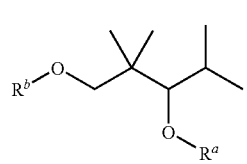

wherein in each case one of the two radicals $R^a$ or $R^b$ represents hydrogen and in each case the other radical $R^a$ or $R^b$ represents an acyl radical having 2 to 6 C atoms,
for reducing an odor
or
as an auxiliary for reducing an odor.

10 Claims, No Drawings

ODOUR-REDUCING SUBSTANCES

CROSS-REFERENCE TO RELATED APPLICATION

This application claims benefit of priority to EP 08 153 042.0, filed on Mar. 19, 2008, which is incorporated herein by reference in its entirety.

The present invention relates to the use of a single alcohol of formula (1) or to a mixture comprising or consisting of two or more different alcohols of formula (1) for reducing an odour, in particular an unpleasant odour, or as an auxiliary (odour neutraliser) for reducing an (unpleasant) odour. The meaning of the two radicals $R^a$ and $R^b$ of the compounds of formula (1) shown here is provided further below:

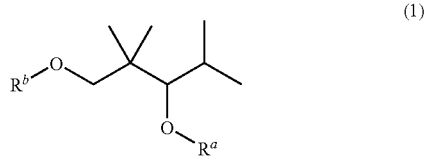

(1)

The invention also relates to selected preparations which comprise, in addition to the one or more alcohols of formula (1) to be used according to the invention, one or more odorous substances and optionally further substances (for example production auxiliaries). For further features of the preparation(s) according to the invention and for preferred embodiment(s) of this/these preparations, see the following description and the accompanying claims.

In the following, a description will also be provided of a method for checking the reduction of an unpleasant odour by a test substance comprising one or more alcohols of formula (1), in which method a malodorous standard mixture comprising or consisting of a substance having an unpleasant odour is compared with a test mixture which also comprises the substance having an unpleasant odour and also the indicated test substance. Further features of this method and preferred embodiments are described further below.

Everyday life frequently presents the problem of (unpleasant) odours which adversely affect the wellbeing of people. Unpleasant odours (within the context of the present text) are in particular odours which originate from human perspiration and excretion, above all sweat, faecal and urine odours, faecal or urine odours of animals, particularly of pets, odours from wet coats of animals, in particular wet coats of dogs or sheep, odours from wet sheep's wool, cooking odours, as produced for example during the preparation of onions, garlic, cabbage or fish, and odours from tobacco smoke, in particular from stale tobacco smoke, mould and refuse. The applications according to the invention relate in particular to the reduction of odours of this type.

Unpleasant odours also arise in many industrially produced basic substances used in cosmetic, body care, household or cleaning products, in particular in basic substances used in detergents, for example for laundry detergents and fabric softeners, or in body care products, for example for soaps and cosmetics.

The use(es) of specific cosmetic preparations, for example hair dyes, hair shaping agents and depilatories also produce unpleasant odours and thus cause upset to people. The applications according to the invention also relate in particular to the reduction of unpleasant odours of this type.

The mentioned odour nuisance or unpleasant odours are caused for the most part by particularly odour-intensive substances, these often only occurring in traces. Substances of this type are, inter alia, nitrogen-containing compounds, such as ammonia and amines, N-heterocycles such as pyridines, pyrazines, indoles etc. and sulphur-containing compounds, such as hydrogen sulphide, mercaptans, sulphides etc. In particular, the reduction of the odours of N- or S-containing compounds of this type is an object of the present invention.

The reduction of odours, in particular unpleasant odours is a problem which is difficult to treat and solve in terms of perfume composition. In particular, the specific character of a respective unpleasant odour greatly restricts the use of diverse preparations, in particular perfumes of the usual different fragrance types. A reduction of this type of unpleasant odours is generally achieved at best using a specifically developed perfume oil which itself has its own quite specific fragrance type. In this case, the unpleasant odour impressions are masked or "covered" by means of substances of (another) pleasant smelling odour.

Therefore, those substances or materials are of great advantage which are able to reduce the intensity of unpleasant odours or even to completely eliminate the unpleasant odour, without themselves being of an appreciable olfactory-perfume intensity. Such (active) substances could advantageously neutralise unpleasant odours without masking the respective unpleasant odour merely by their own specific odour. The use of such (active) substances has or could have the advantage that to fragrance or perfume objects, it is possible to use preparations or products having unpleasant odours, for example perfume oils of any fragrance direction. Consequently, in order to "combat" odour nuisance or unpleasant odours, the consumer can be offered a substantially wider choice of fragrance types.

The literature contains numerous proposals for combating body odour and other unpleasant odours, as shown for example in the following.

EP 0 780 132 describes the control of unpleasant odours, specifically cooking and refuse odours, tobacco odour and the odour from excrement, using specific odorous substance mixtures. The mixtures described here comprise approximately 20 to 60% by weight of musk odorous substances, approximately 30 to 70% by weight of citrus odorous substances and approximately 1 to 20% by weight of peppermint odorous substances.

U.S. Pat. No. 5,559,271 describes, inter alia, vanillin, methyl acetate, isopulegol, menthol, linalool and many other odorous substances which are capable of controlling the unpleasant odour of organic polysulphides.

WO 98/27261 relates to animal litter which has a reduced odour. Mentioned here as a constituent of perfume oils for animal litter which are to have refreshing and deodorising properties are, inter alia, menthyl acetate, vanillin, dihydromyrcenol, eucalyptol, isopulegyl acetate, citronellol, geraniol and benzyl alcohol, in addition to numerous other odorous substances.

WO 01/43784 and U.S. Pat. No. 7,157,411 describe the use of specific esters, in particular isomenthyl esters such as isomenthyl acetate, as odour-reducing substances for reducing the most varied type of unpleasant odours.

EP 1 447 102 proposes mixtures of specific cyclohexylethan-1-yl-esters, in particular the acetate and n-butyrate, to control unpleasant odours.

JP-B1 056 798 describes masking bleaching lye odour using selected odorous substances, including 2,6-dimethyl-4-heptyl acetate and 3,3,5-trimethylcyclohexylisobutyrate.

EP 1 113 105 describes a mixture against human body odour as addition to a perfume. The following (active) constituents are mentioned, inter alia: beta-naphthylmethylether, methyl-beta-naphthylketone, benzylacetone, gamma-methylionone, geranonitrile, ethylenebrassylate, 1-cyclohexadecen-5-one and 1-cycloheptadecen-10-one.

JP 2003113392 describes a composition to be used as an antiperspirant for masking body odour. Used in this composition for perfuming are, for example alpha-pinene, limonene, ethyl acetate, cineol, acetyl cedrene, geraniol, thymol, tetradecanal, amyl salicylate, vanillin, eucalyptus oil, jasmine oil and spearmint oil.

Previous substances, i.e. (odorous) substances or (odorous) substance mixtures which are aimed at an olfactory revaluation of products generally have an unsatisfactory odour reduction of unpleasant odours.

To neutralise or reduce unpleasant odours, odorous substances and odorous substance compositions/mixtures are often used where the development of (odorous) substances and (odorous) substance compositions as well as the checking of the efficacy of these substances in reducing unpleasant odours has hitherto usually been performed by trial and error.

Within the scope of the present text, the concept of neutralising or reducing odours, in particular unpleasant odours is understood as meaning a partial reduction or a complete reduction, i.e. elimination, of (unpleasant) odours by a specific substance, in particular odours of the type of sweat, old fat, old fish, smoke, butyric acid, excrement or similar odours. A substance in this respect is an individual substance or a substance mixture.

A fragrancing or perfuming (of a product) in a narrower sense is to be distinguished in this respect from a neutralisation or reduction of an unpleasant odour and can take place in addition to such a neutralisation/reduction. The term fragrancing or perfuming is understood to mean imparting an odour impression, i.e. an additional olfactory effect which, if appropriate, goes beyond a complete or partial reduction of the unpleasant odour.

Within the scope of the present text, an odorous substance in a wider sense is any substance which evokes an olfactory impression or changes the olfactory perception of another substance due to its own odour. However, in a narrower sense in the context of this invention, an odorous substance is a substance which provokes an olfactory impression, particularly an olfactory impression in people. Accordingly, an odorous substance mixture is a mixture comprising two or more odorous substances in the narrower or wider sense.

In view of the prior art referenced above, it was the primary object of the present invention to provide alternative or improved substances, i.e. substances or substance mixtures, for neutralising or reducing unpleasant odours and preferably additionally for fragrancing or perfuming products, in particular products which have an unpleasant odour.

These substances should preferably satisfy one, more or preferably all the following requirements:
  easy accessibility,
  usability also in a concentrated form,
  substantial or complete colourlessness,
  high stability in the respective product having an unpleasant odour, in particular no occurrence of discolouration and/or separation and/or cloudiness,
  inert behaviour with respect to this/these product(s),
  no toxic and/or allergenic effect on humans,
  slight inherent odour.

Furthermore, the present invention will state preparations which comprise the odour-neutralising or odour-reducing substances. Preparations of this type should preferably be capable of fragrancing or perfuming objects or products, in particular objects or products which have an unpleasant odour, and said odour is to be primarily reduced by using the indicated substances.

Within the scope of the present text, a preparation is itself a product which is produced according to a recipe or a formulation from specific basic materials or basic substances according to a given process. Preparations of this type are produced intentionally (particularly in respect of their composition) and are based on a formulation; they are not naturally occurring (substance) mixtures as can be obtained, for example, by extraction from vegetable starting materials.

In addition, a method should be stated, by which it is possible to assess odour-neutralising or odour-reducing substances which may be concerned in respect of their (unpleasant) odour-reducing property, such that specific substances can be purposefully tested for their suitability for a specific odour-neutralising application.

Further objects on which the present invention is based emerge from the following information and the accompanying claims.

The prior art provided no indication that the compounds or mixtures to be used according to the invention and described in the following can be used as odour-neutralising or odour-reducing substances, in particular as substances reducing an unpleasant odour.

The aforementioned primary object is achieved according to the invention by the use
(i)(a) of a single alcohol of formula (1) or
(i)(b) of a mixture comprising or consisting of two or more different alcohols of formula (1),

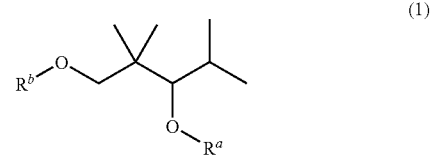

(1)

wherein in each case one of the two radicals $R^a$ or $R^b$ represents hydrogen and in each case the other radical $R^a$ or $R^b$ represents an acyl radical having 2 to 6 C atoms,
for reducing an odour
or
as an auxiliary for reducing an odour.

In the context of the object set, an odour of this type is preferably an unpleasant odour. As already mentioned at the outset, unpleasant odours adversely affect people's wellbeing. An unpleasant odour of this type is preferably an odour from human perspiration and excretion, in particular sweat, faecal and urine odours, i.e. in particular a human body odour, more particularly a human smell of sweat (particularly underarm sweat odour), or a faecal or urine odour from animals, in particular from pets, or an odour of a wet animal coat, in particular the wet coat of dogs or sheep, an odour of wet sheep's wool, or cooking odours, as produced, for example during the preparation of onions, garlic, cabbage or fish, or tobacco smoke odour, in particular stale tobacco smoke, or an odour of mould and/or refuse. In particular, an unpleasant odour of this type is a human sweat odour, toilet odour, in particular human faecal and urine odours, faecal or urine odours of animals, particularly of pets, cooking odours, in particular of old fat, old fish or butyric acid, or smoke, in particular (stale) tobacco smoke.

Further odours which are to be preferably reduced in the context of the use according to the invention are unpleasant odours from industrially produced basic materials used in cosmetic, body care, household or cleaning products (as described in the introduction).

In particular, an unpleasant odour as described above is an odour which is produced during the use of specific cosmetic preparations, for example hair dyes, hair shaping agents and depilatories.

In an application according to the invention, in each case one of the two radicals $R^a$ or $R^b$ preferably represents hydrogen and in each case the other radical $R^a$ or $R^b$ preferably represents an acyl radical having 4 C atoms.

It applies more particularly to an application according to the invention described above that
in alternative (i)(a) the acyl radical having 2 to 6 C atoms of the alcohol or
in alternative (i)(b) the acyl radical having 2 to 6 C atoms of one, two, more or all the alcohols
is selected from the group consisting of acetyl, propionyl, n-butyryl, isobutyryl, crotonyl, n-pentanoyl, isopentanoyl, n-hexanoyl and isohexanoyl, preferably selected from the group consisting of n-butyryl, isobutyryl and crotonyl.

Compounds of formula (1) are monoesters of 2,2,4-trimethylpentane-1,3-diol. Compounds of this type of formula (1) have to some extent already been commercially available for a relatively long time (cf. U.S. Pat. No. 3,329,713) or can be obtained in a known manner by esterification of 2,2,4-trimethylpentane-1,3-diol, as described, for example in Liebigs Ann. 1972, 756, 162-169 or in U.S. Pat. No. 3,408,388. Alternative processes for the production of the compounds of formula (1) are known, for example from U.S. Pat. No. 3,091,632, DE 3403696, U.S. Pat. No. 5,166,413, WO 98/24752 or DE 10207747 and from the literature respectively cited therein or can be carried out according to these processes.

The compounds of formula (1) to be used according to the invention advantageously have only a very weak inherent odour. The (unpleasant) odour to be reduced is thus not primarily masked by a specific inherent odour of the respective alcohol(s) of formula (1). It is true that the working mechanisms of the odour neutralisation which takes place in the context of the present invention have not been conclusively explained. However, the action is presumably based on the fact that in the context of a use according to the invention, an interaction takes place between the alcohols of formula (1) to be used according to the invention and various receptors in the olfactory mucous membrane of the human nose, which presumably results in an (odour) misperception, such that the presently perceived odour impression is no longer associated with the original cause (of an unpleasant odour). The inherent odour of the alcohols of formula (1) to be used according to the invention is preferably so faint or is of such a low (fragrance) intensity that it can hardly be perceived (by humans). These (very faint smelling) alcohols of formula (1) are to be considered in the context of the present invention as (perfuming) auxiliaries. The alcohols of formula (1) to be used according to the invention or corresponding mixtures to be used according to the invention are particularly suitable for reducing an odour, in particular an unpleasant odour (for example in corresponding products, the odour of which is to be neutralised or products to be fragranced), and/or as an auxiliary for reducing an (unpleasant) odour.

Compounds of formula (1) also have the advantage that when they are used, in particular when used according to the invention, they can be combined with the most varied odorous substances and perfume oils, to thus perfume of fragrance objects or products, in particular those with unpleasant odours, with any fragrance direction. Consequently, by virtue of the present invention, when controlling unpleasant odours, a wide selection of fragrance types can be offered to the consumer.

A further preferred embodiment of the present invention relates to a use (as described above) of a mixture comprising or consisting of a first alcohol of formula (1) and a second alcohol of formula (1), wherein
the radical $R^a$ of the first alcohol has the meaning of $R^b$ of the second alcohol and
the radical $R^b$ of the first alcohol has the meaning of $R^a$ of the second alcohol.

The compounds of formulae (1a) and (1b) shown in the following are particularly suitable for the purposes of the present invention. Accordingly, a use according to the invention, as described above, is more preferred, wherein
(i)(a) a single alcohol of formula (1a) or (1b), or
(i)(b) a mixture comprising or consisting of an alcohol of formula (1a) and of an alcohol of formula (1b) is used.

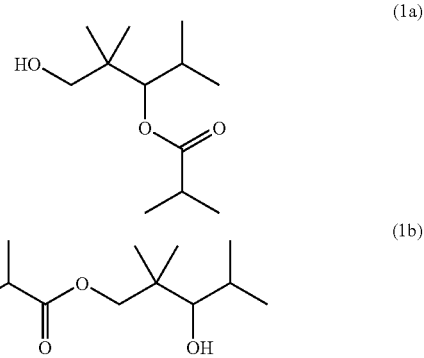

Particularly preferred is a use, as described above, wherein the weight ratio of the first alcohol of formula (1) to the second alcohol of formula (1) is within a range of from 10:1 to 1:10, preferably within a range of from 5:1 to 1:5.

The compounds of formula (1a) and (1b) have particularly good odour-neutralising or odour-reducing properties within the context of the present invention. Therefore, in the context of the present invention, a use according to the invention is more preferred (as described above), wherein a mixture of compounds (1a) and (1b) is used. In a use, as described above, the weight ratio of the two compounds (1a):(1b) is preferably within a range of from 10:1 to 1:10, preferably within a range of from 5:1 to 1:5, more preferably within a range of from 2:1 to 1:3, most preferably within a range of from 3:2 to 1:2.

The compound of formula (1a) (CAS number 18491-15-1) and the compound of formula (1b) (CAS number 77-68-9) are already known per se. Likewise, mixtures of compound (1a) and compound (1b) are known (CAS number 25265-77-4). Mixtures of this type can be prepared, for example as described above. In addition, mixtures of this type are commercially available, for example from the companies BASF, DSM, Eastman or Perstorp.

Yukagaku (1993), 42(1), pages 44-48 discloses the occurrence of 2-methylpropionic acid-3-hydroxy-2,2,4-trimethylpentylester of the above formula (1b) in specific plants of the Polypodiaceae family. The odorous substances hexanal, heptanal, 4-hexen-1-ol, 1-hepten-3-ol, vanillin, cedrol, linalool, beta-ionone, alpha-pinene, isobutylisobutyrate, alpha-terpineol und ethyl cinnamate were also found. The disclosed mixtures are not an object of the present invention. The disclosed mixtures are not preparations within the meaning of the above definition.

Yukagaku (1989), 38(9), pages 689-693, Nippon Nogei Kagaku Kaishi (1989), 63(7), pages 1231-1234 and Nippon Nogei Kagaku Kaishi (1988), 62(12), pages 1763-1768 report on the occurrence of 2-methylpropionic acid-3-hydroxy-2,2,4-trimethylpentylester of the above formula (1b) in different types of beans. Inter alia, odorous substances such as, hexanal, 2-phenylethanol, vanillin, maltol, guaiacol, 4-vinylguiacaol, furfuryl alcohol, furfural, cedrol, butyl butyrate and ethyl cinnamate were also identified. The disclosed mixtures are not an object of the present invention. The disclosed mixtures are not preparations within the meaning of the above definition.

JP 11222574 describes the use of specific compounds also to be used according to the invention, as a constituent in a water-based sealant for porous building materials. JP 2003171635 describes the use of specific compounds also to be used according to the invention, as a constituent in an adhesive for building materials. However, the present invention does not relate to any of these disclosed compounds and mixtures. The use of the compounds of formula (1) to be used according to the invention as a constituent of an adhesive or sealant for (porous) building materials is, however, generally not preferred in the context of the present invention, in particular the use as a constituent in a water-based sealant for porous building materials according to JP 11222574 or as a constituent in an adhesive for building materials according to JP 2003171635.

FR 2867972 describes the use of specific compounds to be used according to the invention in nail varnish. A nail varnish of this type is not an object of the present invention. The use in varnishes, particularly in nail varnish is generally not preferred in the context of the present invention.

WO 2004/062363 describes the use of 2-methylpropionic acid-3-hydroxy-2,2,4-trimethylpentylester of the above formula (1b) in a mixture to form a biocidal film on a surface. This mixture can optionally contain a perfume oil (fragrance), which is not specified in more detail in this document. The mixtures described in WO 2004/062363, in particular the mixtures according to Example 1 of WO 2004/062363 are not an object of the present invention. The use of alcohols of formula (1), in particular of formula (1b) to be used according to the invention in a mixture to form a biocidal film on a surface, in particular in such a mixture comprising a film-forming agent is generally not preferred in the context of the present invention.

WO 95/21606 mentions a compound of formula (1) where $R^b$=isobutyryl and $R^a$=H (3-hydroxy-2,2,4-trimethylpentyl-isobutyrate) as starting material for the preparation of unsaturated 2,2,4-trimethylpent-3-en-1-yl-isobutyrate by dehydration. In this connection, it is specified here that specific 2,2,4-trimethylpenten-1-yl-esters, for example the mentioned unsaturated isobutyrate, can be used as odorous substances and flavouring substances. The mentioned butyrate has a fruity citrus, green, flowery smell. The mixtures disclosed in WO 95/21606 containing compounds of formula (1) and uses of compounds of formula (1) are not an object of the present invention. Mixtures comprising 3-3-hydroxy-2,2,4-trimethylpentylisobutyrate and 2,2,4-trimethylpent-3-en-1-yl-isobutyrate are generally not preferred in the context of the present invention.

In U.S. Pat. No. 5,942,467, according to an embodiment mentioned therein, the substance 2-methylpropionic acid-3-hydroxy-2,2,4-trimethylpentylester of the above formula (1b) is proposed as a constituent of drilling fluids. The present invention does not relate to any use of alcohols of formula (1) to be used according to the invention as a constituent of drilling fluids, in particular not as a constituent of drilling fluids according to U.S. Pat. No. 5,942,467. The mixtures disclosed therein are not an object of the present invention.

Food Res. Int. 2001, 34, 473-481 and J. Food Science 2002, 67, 848-854 reports on the contribution of 2-methylpropionic acid-3-hydroxy-2,2-dimethyl-1-(1-methylethyl)-propylester of the above formula (1a) to flavourings of cooked prawns or cooked calamari. The mixtures disclosed therein are not an object of the present invention. In the context of the present invention, a use of alcohols of formula (1), in particular of formula (1a) to be used according to the invention in mixtures based on cooked prawns or cooked calamari is not preferred. Instead, in the context of the present invention, those uses are preferred which are aimed at an odour-reducing or odour-neutralising action as described above and also further below.

The cited documents give no indication that the compounds or mixtures to be used according to the invention can be used as odour-neutralising or odour-reducing substances, and in particular give no indication that they can be used as a substance which reduces an unpleasant odour or as an auxiliary for reducing an (unpleasant) odour (as described above).

The experiments carried out in the context of the present invention (cf. in this respect the Examples below) showed that in the context of a use according to the invention, the respective alcohols of formula (1) or corresponding mixtures are particularly suitable for neutralising diverse and structurally very different substances which have an unpleasant odour or which, as a constituent, contribute to an unpleasant odour, i.e. for reducing in particular the unpleasant odour caused by these substances. Starting from the information in U.S. Pat. No. 5,538,719, this was unexpected, since it is described there that a mutual odour masking is caused by structurally similar compounds (cross adaption). In this context, the masking of 3-methyl-2-hexenic acid with a structurally similar ester is described there. Accordingly, it was particularly surprising that the compounds to be used according to the invention are suitable, in spite of the structural differences of the substances which cause the different (unpleasant) odour impressions, for reducing the (unpleasant) odours caused by such substances or neutralising the odour of such substances.

The compounds of formula (1) or corresponding mixtures to be used according to the uses of the invention (as described above) are therefore particularly suitable for the purposes of the present invention for reducing an (unpleasant) odour or as an auxiliary for reducing an (unpleasant) odour. The alcohols of formula (1) or corresponding mixtures to be used according to the invention are particularly suitable (for example in a preparation according to the invention described below) for reducing an unpleasant odour or reducing, as an auxiliary (for example as a constituent of a preparation (according to the invention) during use of said preparation) an unpleasant odour. See below for preparations according to the invention.

As our own experiments in the context of the present invention have surprisingly shown, the diesters of 2,2,4-trimethylpentane-1,3-diol (i.e. $R^a$ and $R^b$ both represent an acyl radical) have, compared to the monoesters to be used according to the invention, significantly poorer odour-neutralising or odour-reducing properties, thus for example for the di-isobutyrate of 2,2,4-trimethylpentane-1,3-diol.

The alcohols of formula (1) or corresponding mixtures to be used according to the invention can form preparations according to the invention when combined with further substances. Within the scope of the present text, a preparation (according to the invention) is defined as described above.

A preparation of this type preferably consists of or comprises (i)(a) a single alcohol of formula (1) (as defined above), or
(i)(b) a mixture comprising or consisting of two or more different alcohols of formula (1) (as defined above),
and
(ii) one or more, preferably two, three, four, five, six, seven, eight, nine, ten or more odorous substances, these substances not being compounds of formula (1),
with the proviso that this preparation is not a preparation comprising 3-hydroxy-2,2,4-trimethylpentylisobutyrate and 2,2,4-trimethylpent-3-en-1-yl-isobutyrate.

A preparation of this type is advantageously particularly very suitable for reducing an unpleasant odour. In addition to this primary purpose, the preparations according to the invention are particularly also suitable for fragrancing or perfuming objects or products in the sense of the above-mentioned definition.

According to a further aspect of the present invention, a preparation according to the invention is preferably a perfume oil. Perfume oils usually comprise or consist of synthetic or natural (preferably) taste and odour-neutral carrier oils which contain fragrances or odorous substances (for example from a specific plant) as artificial or natural substances in a highly concentrated form (and optionally perfuming solvents and/or auxiliaries). Thus, perfume oils are frequently used for fragrancing applications. Using perfume oils, perfumes for example are produced by introducing them into (for example alcoholic) solutions which, during evaporation, "entrain" the fragrances or odorous substances and thus impart to the olfactory organ of the user, i.e. the person, the sensation of a specific odour. Mixtures of this type can be, for example a perfume, eau de perfume or eau de toilette. Furthermore, perfume oils are used to produce a specific fragrance in living spaces, as for example when used in fragrance lights, atomisers or diffusers. In addition, perfume oils can, however, also be used in countless other articles or preparations, for example from shoe polish to shampoos, sanitary towels to WC cleaners, face creams to washing powders and cat litter.

Examples of odorous substances which can advantageously be used as a constituent of a preparation according to the invention, in particular of a perfume oil according to the invention are found, for example in S. Arctander, Perfume and Flavor Chemicals, Vol. I and II, Montclair, N.J., 1969, self-published or H. Surburg, J. Panten, Common Fragrance and Flavor Materials, 5$^{th}$ Ed., Wiley-VCH, Weinheim 2006.

Preferred ethereal oils, concretes, absolutes, resins, resinoids, balsams and/or tinctures which can be a constituent of a preparation according to the invention, in particular of a perfume oil according to the invention are preferably to be selected from the group consisting of: ambra tincture; amyris oil; angelica seed oil; angelica root oil; aniseed oil; valerian oil; basil oil; wood moss absolute; bay oil; mugwort oil; benzoin resin; bergamot oil; beeswax absolute; birch tar oil; bitter almond oil; savoury oil; bucco leaf oil; cabreuva oil; cade oil; calmus oil; camphor oil; cananga oil; cardamom oil; cascarilla oil; cassia oil; cassia absolute; castoreum absolute; cedar leaf oil; cedar wood oil; cistus oil; citronella oil; lemon oil; copaiva balsam; copaiva balsam oil; corianda oil; costus root oil; cumin oil; cypress oil; Davana oil; dill herb oil; dill seed oil; eau de brouts absolute; oakmoss absolute; elemi oil; estragon oil; eucalyptus citriodora oil; eucalyptus oil; fennel oil; spruce needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; camomile blue oil; camomile Roman oil; carrot seed oil; cascarilla oil; pine needle oil; spearmint oil; caraway oil; labdanum oil labdanum absolute; labdanum resin; lavandin absolute; lavandin oil; lavender absolute; lavender oil; lemongrass oil; lovage oil; distilled lime oil; pressed lime oil; linaloe oil; litsea cubeba oil; bayleaf oil; mace oil; marjoram oil; mandarin oil; massoi bark oil; mimosa absolute; musk seed oil; musk tincture; clary sage oil; nutmeg oil; myrrh absolute; myrrh oil; myrtenol; clove leaf oil; clove flower oil; neroli oil; olibanum absolute; olibanum oil; opopanax oil; orange-flower absolute; orange oil; origanum oil; palmarosa oil patchouli oil; perilla oil; peruvian balsam oil; parsley leaf oil; parsley seed oil; petitgrain oil; peppermint oil; pepper oil; pimenta oil; pine oil; pennyroyal oil; rose absolute; rosewood oil; rose oil; rosemary oil; dalmation sage oil; Spanish sage oil; sandalwood oil; celery seed oil; spike lavender oil; Japanese anise oil; styrax oil; tagetes oil; fir needle oil; teatree oil; turpentine oil; thyme oil; Tolu balsam; tonka absolute; tuberose absolute; vanilla abstract; violet leaf absolute; verbena oil; vetiver oil; juniper oil; wine lees oil; absinthe oil; wintergreen oil; ylang oil; hyssop oil; civet absolute; cinnamon leaf oil; cinnamon bark oil.

Preferred individual odorous substances which are preferably used as a constituent of a preparation according to the invention, in particular of a perfume oil according to the invention, are selected from the group:

of hydrocarbons, preferably 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

of aliphatic alcohols, preferably hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

of aliphatic aldehydes and acetals thereof, preferably hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanaldiethylacetal; 1,1-dimethoxy-2,2,5-trimethyl-4-hexene; citronellyl oxyacetaldehyde; 1-(1-methoxy-propoxy)-(E/Z)-3-hexene;

of aliphatic ketones and oximes thereof, preferably 2-heptanone; 2-octanone; 3-octanone; 2-nonanone; 5-methyl-3-heptanone; 5-methyl-3-heptanonoxime; 2,4,4,7-tetramethyl-6-octen-3-one; 6-methyl-5-hepten-2-one;

of aliphatic sulphur-containing compounds, preferably 3-methylthio-hexanol; 3-methylthiohexylacetate; 3-mercaptohexanol; 3-mercaptohexylacetate; 3-mercaptohexylbutyrate; 3-acetylthiohexylacetate; 1-menthene-8-thiol;

of aliphatic nitriles, preferably 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

of esters of aliphatic carboxylic acids, preferably (E)- and (Z)-3-hexenylformiate; ethylacetoacetate; isoamylacetate; hexylacetate; 3,5,5-trimethylhexylacetate; 3-methyl-2-butenylacetate; (E)-2-hexenylacetate; (E)- and (Z)-3-hexenylacetate; octylacetate; 3-octylacetate; 1-octen-3-ylacetate; ethylbutyrate; butylbutyrate; isoamylbutyrate; hexylbutyrate; (E)- and (Z)-3-hexenyl-isobutyrate; hexylcrotonate; ethylisovalerianate; ethyl-2-methylpentanoate; ethylhexanoate; allylhexanoate; ethylheptanoate; allylheptanoate; ethyloctanoate; ethyl-(E,Z)-2,4-decadienoate; methyl-2-octinate; methyl-2-noninate; allyl-2-isoamyloxyacetate; methyl-3,7-dimethyl-2,6-octadienoate; 4-methyl-2-pentyl-crotonate;

of acyclic terpene alcohols, preferably citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerianates, pentanoates, hexanoates, crotonates, tiglinates and 3-methyl-2-butenoates thereof;

of acyclic terpene aldehydes and ketones, preferably geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal;

of cyclic terpene alcohols, preferably isopulegol; alpha-terpineol; terpinenol-4; menthan-8-ol; menthan-1-ol; menthan-7-ol; borneol; isoborneol; linalooloxide; nopol; cedrol; ambrinol; vetiverol; guaiol; and formates, acetates, propionates, isobutyrates, butyrates, isovalerianates, pentanoates, hexanoates, crotonates, tiglinates and 3-methyl-2-butenoates thereof; menthylformiate; menthylpropionate; menthylbutyrate; menthylisobutyrate; menthylisovalerianate; menthylhexanoate; menthylcrotonate; menthyltiglinate;

of cyclic terpene aldehydes and ketones, preferably menthone; isomenthone; 8-mercaptomenthan-3-one; carvone; camphor; fenchone; alpha-ionons; beta-ionone; beta-n-methylionone; beta-isomethylionone; alpha-iron; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (methyl cedryl keton);

of cyclic alcohols, preferably 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

of cycloaliphatic alcohols, preferably alpha,3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

of cyclic and cycloaliphatic ethers, preferably cineol; cedryl methyl ether; cyclododecyl methyl ether; 1,1-dimethoxycyclododecane; (ethoxymethoxy)cyclododecane; alpha-cedrenepoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

of cyclic and macrocyclic ketones, preferably 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

of cycloaliphatic aldehydes, preferably 2,4-dimethyl-3-cyclohexencarbaldehyde; 2-methyl-4-(2,2,6-trimethyl-cyclohexen-1-yl)-2-butenal; 4-(4-hydroxy-4-methylpentyl)-3-cyclohexencarbaldehyde; 4-(4-methyl-3-penten-1-yl)-3-cyclohexencarbaldehyde;

of cycloaliphatic ketones, preferably 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphtalenyl methyl ketone; methyl-2,6,10-trimethyl-2,5,9-cyclododecatrienyl ketone; tert.-butyl-(2,4-dimethyl-3-cyclohexen-1-yl) ketone;

of esters of cyclic alcohols, preferably 2-tert-butylcyclohexylacetate; 4-tert-butylcyclohexylacetate; 2-tert-pentylcyclohexylacetate; 4-tert-pentylcyclohexylacetate; 3,3,5-trimethylcyclohexylacetate; decahydro-2-naphthylacetate; 2-cyclopentylcyclopentylcrotonate; 3-pentyltetrahydro-2H-pyran-4-ylacetate; decahydro-2,5,5,8a-tetramethyl-2-naphthylacetate; 4,7-methano-3a,4,5,6,7,7a-hexahydro-5, or 6-indenylacetate; 4,7-methano-3a,4,5,6,7,7a-hexahydro-5, or 6-indenylpropionate; 4,7-methano-3a,4,5,6,7,7a-hexahydro-5, or 6-indenylisobutyrate; 4,7-methanooctahydro-5, or 6-indenylacetate;

of esters of cycloaliphatic alcohols, preferably 1-cyclohexylethylcrotonate;

of esters of cycloaliphatic carboxylic acids, preferably allyl-3-cyclohexylpropionate; allylcyclohexyloxyacetate; cis- and trans-methyldihydrojasmonate; cis- and trans-methyljasmonate; methyl-2-hexyl-3-oxocyclopentanecarboxylate; ethyl-2-ethyl-6,6-dimethyl-2-cyclohexenecarboxylate; ethyl-2,3,6,6-tetramethyl-2-cyclohexenecarboxylate; ethyl-2-methyl-1,3-dioxolan-2-acetate;

of araliphatic alcohols, preferably benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol-1-ol; 3-methyl-5-phenylpentanol; 3-phenyl-2-propen-1-ol; 4-methoxybenzyl alcohol; 1-(4-isopropylphenyl)ethanol;

of esters of araliphatic alcohols and aliphatic carboxylic acids, preferably benzyl acetate; benzyl propionate; benzyl isobutyrate; benzyl isovalerianate; 2-phenylethyl acetat; 2-phenylethyl propionate; 2-phenylethyl isobutyrat; 2-phenylethyl isovalerianate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

of araliphatic ethers, preferably 2-phenylethyl methyl ether; 2-phenylethyl isoamyl ether; 2-phenylethyl-1-ethoxyethyl ether; phenylacetaldehyde dimethyl acetal; phenylacetaldehyde diethyl acetal; hydratropaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

of aromatic and araliphatic aldehydes, preferably benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-

(4-isopropylphenyl)propanal; 2-methyl-3-(4-tert.-butylphenyl)propanal; 2-methyl-3-(4-isobutylphenyl)propanal; 3-(4-tert.-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

of aromatic and araliphatic ketones, preferably acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

of aromatic and araliphatic carboxylic acids and esters thereof, preferably benzoic acid; phenylacetic acid; methyl benzoate; ethyl benzoate; hexyl benzoate; methyl phenylacetate; ethyl phenylacetate; geranyl phenylacetate; phenylethyl-phenylacetate; methyl cinnmate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl-2,4-dihydroxy-3,6-dimethylbenzoate; ethyl-3-phenylglycidate; ethyl-3-methyl-3-phenylglycidate;

of nitrogen-containing aromatic compounds, preferably 2,4,6-trinitro-1,3-dimethyl-5-tert.-butylbenzene; 3,5-dinitro-2,6-dimethyl-4-tert.-butylacetophenone; cinnamic acid nitrile; 3-methyl-5-phenyl-2-pentenoic acid nitrile; 3-methyl-5-phenylpentanoic acid nitrile; methyl anthranilate; methyl-N-methylanthranilate; Schiff bases of methyl anthranilate with 7-hydroxy-3,7-dimethyloctanal, 2-methyl-3-(4-tert.-butylphenyl)propanal or 2,4-dimethyl-3-cyclohexenecarbaldehyde; 6-isopropylquinoline; 6-isobutylquinoline; 6-sec.-butylquinoline; 2-(3-phenylpropyl)pyridine; indole; skatole; 2-methoxy-3-isopropylpyrazine; 2-isobutyl-3-methoxypyrazine;

of phenols, phenylethers and phenyl esters, preferably estragole; anethole; eugenole; eugenyl methyl ether; isoeugenole; isoeugenyl methyl ether; thymole; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

of heterocyclic compounds, preferably 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of lactones, preferably 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,13-tridecandioate; coumarin; 2,3-dihydrocoumarin; octahydrocoumarin.

A preparation according to the invention as described above is preferably
(a) a mixture for reducing an odour
or
(b) a mixture in which, when individual constituents are used, they generate an unpleasant odour which is reduced by the presence of alcohol(s) of formula (1), or
(c) a mixture in which one, two or more of the odorous substances of group (ii) have an unpleasant odour which is reduced by the presence of alcohol(s) of formula (1),
the unpleasant odour in the alternatives (b) and (c) preferably being selected from the group consisting of: human sweat odour, toilet odour, in particular human faecal and urine odours, faecal or urine odours of animals, particularly of pets, odours from wet coats of animals, in particular wet coats of dogs or sheep, odours from wet sheep's wool, cooking odours, in particular of old fat, old fish or butyric acid, smoke, in particular (stale) tobacco smoke.

However, further unpleasant odours (as described above) can also be contained in a mixture of this type or can develop during use.

Accordingly, a preparation of the invention according to the first alternative (a) is a mixture for reducing an odour, in particular an unpleasant odour. This means that a mixture of this type preferably comprises, in addition to the one or more alcohols of formula (1) and the one or more odorous substances, no (further) substance which has an unpleasant odour. When a mixture of this type according to alternative (a) is brought into contact with a substance of a specific (unpleasant) odour or during the fragrancing or perfuming of an object or product, said mixture serves to reduce a (preferably unpleasant) odour as defined above.

According to alternative (b), a mixture according to the invention is specified which already comprises individual constituents which generate (during use) an unpleasant odour. In this case, the purpose of the mixture according to the invention is to reduce this developing unpleasant odour by means of the alcohols of formula (1) contained in such a mixture.

Alternative (c) makes it clear that a preparation according to the invention comprising one or more odorous substances (as described above) according to a preferred embodiment is a mixture in which one, two or more of the contained odorous substances of group (ii) already have an unpleasant odour; an unpleasant odour of this type is reduced by the alcohols of formula (1) to be used according to the invention.

For the purposes of the present invention, it is particularly preferred if, in a preparation according to the invention as described above, in particular such a preparation selected from the group of cosmetic, body care, household and cleaning products, but most particularly in a perfume oil according to the invention, the ratio of the total amount of compounds of formula (1) to the total amount of odorous substances based on the weight is preferably in a range of from 10:1 to 1:50, preferably in a range of from 5:1 to 1:30, more preferably in a range of from 2:1 to 1:20, and most preferably in a range of from 3:2 to 1:10. Also for the purposes of this calculation, the compounds of formula (1) are not considered as odorous substances.

In the context of our own experiments, it has been found that preparations according to the invention as described above, in particular perfume oils according to the invention are particularly suitable for the purposes of the present invention when the one or more or all the odorous substances contained in a preparation of this type are selected from the group (B), preferably from the group (B'), as defined in the following. A combination of this type results in an overall improved odour-neutralising or odour-reducing effect (and optionally by the odorous substances contained, in an odour-masking effect). Accordingly, a further aspect of the present invention relates to a preparation as described above, where one, more or all odorous substances are preferably selected from group (B) (in this respect, to some extent product names customary within the industry and registered trade names of different companies are stated):
alpha-hexylcinnamaldehyde, 2-phenoxyethylisobutyrate (phenirate), dihydromyrcenol (2,6-dimethyl-7-octen-2-ol), methyldihydrojasmonate (preferably with a content of cis-isomers >60% by weight (hedione, hedione HC)), 4,6,6,7,8,8-hexamethyl-1,3,4,6,7,8-hexahydrocyclopenta[g]benzopyrane (galaxolide), tetrahydrolinalool (3,7-dimethyloctan-3-ol), ethyllinalool, benzylacetate, benzylsalicylate, 2-methyl-3-(4-tert-butyl-phenyl)propanal (lilial), cinnamyl alcohol, 4,7-methano-3a,4,5,6,7,7a-hexahydro-5-indenylacetate and/or 4,7-methano-3a,4,5,6,7,7a-hexahydro-6-indenylacetate (herbaflorat), styrolylacetate (1-phenylethylacetate), octahydro-2,3,8,8-tetramethyl-2-acetonaphthone and/or 2-acetyl-1,2,3,4,6,7,8-octahydro-2,3,8,8-tetramethylnaphtaline (iso E super), hexylsalicylate, 4-tert.-butylcyclohexylacetate (oryclon), 2-tert.-butylcyclohexylacetate (agrumex HC), alpha-ionone (4-(2,2,6-trimethyl-2-cyclohexen-1-yl)-3-buten-2-one), coumarin, terpinylacetate, 4-(4-hydroxy-4-methylpentyl)-3-cyclohexenecarboxaldehyde (lyral), alpha-amylcinnamaldehyd, (E)- and/or (Z)-3-methylcyclopentadec-5-enone (muscenone), 15-pentadec-11-enolide and/or 15-pentadec-12-enolide (globalide), 15-cyclopentadecanolide (macrolide), cyclohexadecanone (isomuscone), 1-(5,6,7,8-tetrahydro-3,5,5,6,8,8-hexamethyl-2-naphthalenyl)ethanone (tonalide), 2-isobutyl-4-methyltetrahydro-2H-pyran-4-ol (florol), 2-ethyl-4-(2,2,3-trimethyl-3-cyclopenten-1-yl)-2-buten-1-ol (sandolene), menthol (preferably l-menthol or racemic menthol, more preferably l-menthol), eucalyptol (1,8-cineol), anethol, geraniol, nerol, citronellol, linalylacetate, 2,2-dimethyl-3-(3-methylphenyl)-propanol (majantol), rose oxide (4-methyl-2-(2-methyl-1-propenyl)tetrahydropyrane), allyl heptanoate, 4-methylacetophenone, timberol (1-(2,2,6-trimethylcyclohexyl)hexan-3-ol), floropal (2,4,6-trimethyl-4-phenyl-1,3-dioxane), benzyl acetone, methyl cinnamate, 3a,6,6,9a-tetramethyldodecahydronaphtho[2,1-b]furane (ambroxide), 2-methyl-5-phenylpentan-1-ol (rosaphen), 2-phenylethanol, linalool.

It preferably applies to a preparation according to the invention that if the odorous substances 2-phenylethanol and/or linalool (as in particular from group B)) are selected, i.e. are contained in a preparation according to the invention, the preparation also contains at least one further odorous substance of group (B).

However, a preparation according to the invention as described above is particularly preferred wherein one, two, more or all odorous substances are selected from group (B'), consisting of:
alpha-hexylcinnamaldehyd, 2-phenoxyethylisobutyrate, dihydromyrcenol, methyldihydrojasmonate, 4,6,6,7,8,8-hexamethyl-1,3,4,6,7,8-hexahydrocyclopenta[g]benzopyrane, tetrahydrolinalool, benzyl acetat, 2-methyl-3-(4-tert-butyl-phenyl)propanal, cinnamyl alcohol, 1-phenylethylacetate, octahydro-2,3,8,8-tetramethyl-2-acetonaphthone, 2-acetyl-1,2,3,4,6,7,8-octahydro-2,3,8,8-tetramethylnaphtaline, 4-tert.-butylcyclohexylacetate, 2-tert.-butylcyclohexylacetate, alpha-ionone, terpinylacetate, 4-(4-hydroxy-4-methylpentyl)-3-cyclohexenecarboxaldehyde, alpha-amylcinnamaldehyde, 15-pentadec-11-enolide, 15-pentadec-12-enolide, 15-cyclopentadecanolide, cyclohexadecanone, 1-(5,6,7,8-tetrahydro-3,5,5,6,8,8-hexamethyl-2-naphthalenyl)ethanone, 2-ethyl-4-(2,2,3-trimethyl-3-cyclopenten-1-yl)-2-buten-1-ol, menthol, eucalyptol, anethol, geraniol, nerol, citronellol, linalyl acetate, 2,2-dimethyl-3-(3-methylphenyl)-propanol, rose oxide, allylheptanoate, 4-methylacetophenone, timberol (1-(2,2,6-trimethylcyclohexyl)hexan-3-ol), benzyl acetone, methyl cinnamate, 3a,6,6,9a-tetramethyldodecahydronaphtho[2,1-b]furane, 2-methyl-5-phenylpentan-1-ol, 2-phenylethanol, linalool.

It preferably applies to a preparation according to the invention that if the odorous substances 2-phenylethanol and/or linalool (as in particular from group (B) or (B')) are selected, the preparation also contains at least one further odorous substance of group (B').

According to a particularly preferred embodiment, in a preparation according to the invention as described above, the alcohols of formula (1) to be used according to the invention or corresponding mixtures are combined with one or more, preferably with two, three, four, five or more odorous substances of group (B), preferably group (B'), as a combination of this type exhibits a particularly pronounced odour-neutralising or odour-reducing effect. As already mentioned, the odorous substances contained in the preparation have a significant odour-masking effect with respect to an (unpleasant) odour to be reduced, compared to the alcohols of formula (1) to be used according to the invention. With such a combination, it was possible within the scope of our own experiments, to observe not only additive, but also synergistically intensified effects in respect of the odour reduction, in particular in the above-mentioned (particularly) preferred weight ratios of compounds of formula (1) and odorous substances, in particular odorous substances of group (B) or (B').

In preparations according to the invention comprising one or more of the odorous substances of group (B) or (B'), in particular in such cosmetic, body care, household and cleaning products, but particularly in such perfume oils according to the invention, the above details concerning preferred weight ratios apply accordingly, but in particular the ratio of the total amount of compounds of formula (1) to the total amount of odorous substances of group (B) of (B') based on the weight is preferably in a range of from 12.5:1 to 1:40, preferably in a range of from 6.25:1 to 1:24, more preferably in range of from 2.5:1 to 1:16, and most preferably in a range of from 3.75:2 to 1:8.

In a preparation according to the invention as described above or in the following, the total amount of alcohols of formula (1) is preferably in a range of from 0.01 to 10% by weight, preferably in a range of from 0.025 to 5% by weight, more preferably in a range of from 0.05 to 2% by weight, in each case based on the overall weight of the preparation.

According to a further preferred embodiment of a preparation according to the invention (as described above), the preparation also comprises (iii) one, two three or more auxiliaries termed "production auxiliaries" in the following, selected from the group (H) consisting of dipropylene glycol (DPG), diethylphthalate (DEP), triethylcitrate (TEC), isopropylmyristate (IPM) and benzyl benzoate (BB). The term "production auxiliaries" designates, within the scope of the present text, substances which during evaporation "entrain" odorous substances and thus impart to the olfactory organ of the user, i.e. the person, the sensation of a specific odour, and/or substances which, in the event of non-solubility of one or more odorous substances, are required or used, for example as solubilisers, and/or substances which are used to ensure or achieve a specific viscosity of the finished product, and/or substances which are used to dissolve solid odorous substances for the production of a preparation (according to the invention), etc. Accordingly, to achieve a further improved efficacy of the compounds of formula (1) to be used according to the invention, preparations according to the invention, in particular perfume oils or other preferred preparations described above, comprise one, two, three or more production auxiliaries, preferably selected from the group of the production auxiliaries mentioned above. A preparation of this type preferably comprises two, three or more production auxiliaries of group (H). The information provided above applies to the selection of the compounds of formula (1) contained in such a preparation and to the selection of the odorous substances which are contained.

Particularly preferred preparations, in particular perfume oils therefore contain, in addition to the one or more alcohols of formula (1) to be used according to the invention, at least one odorous substance of group (B), preferably group (B'), and at least one production auxiliary of group (H). Particularly preferred are preparations (as described above), preferably in an embodiment stated above as being preferred of the present invention, comprising two or more odorous substances of group (B), more preferably of group (B'), and/or two or more production auxiliaries, preferably selected from group (H).

Accordingly, a further aspect of the present invention relates to a preparation (as described above), comprising
(a) one or more odorous substances of group (B) or (B') and one or more production auxiliaries of group (H)
or
(b) two or more odorous substances of group (B) or (B') and/or two or more production auxiliaries of group (H).

As already mentioned, cosmetic, body care, household and cleaning products are particularly preferred as preparations according to the invention (as described above). Therefore, a preparation according to the invention as described above is preferably a preparation selected from the group consisting of cosmetic, body care, household and cleaning products. A product of this type (according to the invention) can also comprise a perfume oil (according to the invention) described above. Thus, such products either consist of a preparation according to the invention (as described above) or comprise such a preparation.

Preparations which are not according to the invention or are not preferred according to the invention or in particular mixtures which are not preferred are stated in the information provided further above.

By means of a preparation according to the invention as described above, another product or object which has an unpleasant odour can advantageously be perfumed or fragranced in any manner and in so doing, the intensity of the unpleasant odour(s) is reduced and the unpleasant odour impressions are only perceived (by a person) in a reduced form or are no longer perceived at all. To achieve this effect, i.e. to reduce the unpleasant odours, excessively high quantities of odorous substances are not required, since the unpleasant odours (as described above) are primarily reduced by the compound or compounds of formula (1) contained in the preparation.

According to a preferred embodiment, the compounds of formula (1) to be used according to the invention are adsorbed on a carrier which ensures a fine distribution of the compounds in the product or in the preparation and also ensures a controlled release during use. Carriers of this type can be porous inorganic materials, such as silica gels, zeolites, gypsum, clay, clay granules, gas concrete etc. or organic materials such as wood and cellulose-based materials.

The compounds of formula (1) or corresponding mixtures to be used according to the invention can also be microencapsulated, spray-dried, inclusion complexes or extrusion products and can be added in this form to a product, in particular to a product, the odour of which is to be improved by a reduction of an unpleasant odour or to a product to be perfumed.

If required, the properties of such compounds of formula (1) which are thus modified and are to be used according to the invention can be further optimised in respect of a more targeted release by a so-called "coating" operation using suitable materials, for which purpose waxy plastics materials, for example polyvinyl alcohol are preferably used.

The compounds of formula (1) to be used according to the invention can be micro-encapsulated, for example by the so-called coacervation process using capsule materials, for example consisting of polyurethane-type materials or soft gelatins. Spray-dried compounds of formula (1) can be produced, for example by spray drying a substance to be used according to the invention, i.e. an emulsion or dispersion containing an alcohol of the compound of formula (1) or a corresponding mixture, it being possible to use as carrier modified starches, proteins, dextrin and/or vegetable gums. Inclusion complexes can be produced, for example by introducing dispersions which are compounds of formula (1) or corresponding mixtures to be used according to the invention or which comprise said compounds or mixtures, and cyclodextrins or urea derivatives into a suitable solvent, for example water. Extrusion products can be produced by melting the compound(s) of formula (1) or corresponding mixtures to be used according to the invention with a suitable waxy material and by extrusion with subsequent solidification, optionally in a suitable solvent, for example isopropanol.

The compounds of formula (1) or corresponding mixtures to be used according to the invention can be used in many preparations or products, in which case they are preferably combined with one or more of the following auxiliaries or active ingredients:

Preservatives, abrasives, anti-acne agents, anti-aging agents, ant-bacterial agents, anti-cellulite agents, anti-dandruff agents, anti-inflammatory agents, irritation-preventing agents, irritation-inhibiting agents, antimicrobial agents, antioxidants, astringents, sweat-inhibiting agents, antiseptic agents, antistatics, binders, buffers, support materials, chelating agents, cell stimulants, cleansing agents, care agents, depilatories, surface-active substances, deodorising agents, antiperspirants, softeners, emulsifiers, enzymes, ethereal oils, fibres, fixers, foaming agents, foam stabilisers, anti-foam substances, foam boosters, fungicides, gelling agents, gel-forming agents, hair care agents, hair shaping agents, hair smoothing agents, moisturisers, damping substances, moisture-retaining substances, bleaching agents, (textile) reinforcing agents, stain removing agents, optical brighteners, impregnating agents, dirt repelling agents, friction reducing agents, lubricants, moisturising creams, ointments, opacifiers, plasticisers, covering agents, polish, brighteners, polymers, powders, proteins, moisturising agents, abrasive agents, silicones, skin calming agents, skin cleansing agents, skin care agents, skin healing agents, skin lightening agents, skin protecting agents, skin softening agents, cooling agents, skin cooling agents, warming agents, skin warming agents, stabilisers, UV absorbing agents, UV filters, laundry detergents, fabric softeners, suspending agents, skin tanning agents, thickening agents, vitamins, oils, waxes, fats, phospholipids, saturated fatty acids, mono- or polyunsaturated fatty acids, α-hydroxy acids, polyhydroxy fatty acids, liquefiers, dyes, colour-protecting agents, pigments, anticorrosives, aromas, flavourings, perfumes, polyols, surfactants, electrolytes, organic solvents or silicone derivatives.

Preferred products or preparations are perfume extracts, eau de parfum, eau de toilette, aftershave lotions, eau de cologne, pre-shave products, splash colognes and perfumed freshen-up wipes and perfumed cleaning agents or acidic, alkaline and neutral cleaning agents to be perfumed, for example floor cleaners, window cleaners, dishwashing detergents, bath and sanitary cleaners, soft scrub cleaners, solid and liquid WC cleaners, WC sticks, WC blocks (liquid or solid), pulverulent and foam carpet cleaners, liquid detergents, pulverulent detergents, laundry pre-treatment agents such as bleaching agents, soaking agents and stain removers, fabric softeners, laundry soap, washing tablets, disinfectants, surface disinfectants and air fresheners in liquid or gel-type form or applied to a solid carrier, particularly for deodorising extracted air from air conditioning systems and industrial processes, and air fresheners in the form of aerosol or pump sprays, waxes and polishes such as furniture polish, floor waxes, shoe polish, reinforcing, impregnating or deodorising fabric treatment agents, nappies, sanitary towels, panty liners, plasters and body care compositions, for example solid and liquid soaps, shower gels, shampoos, shaving soaps, shaving foams, bath oils, damp cleansing wipes, cosmetic oil-in-water, water-in-oil and water-in-oil-in-water emulsions, for example skin creams and lotions, face creams and lotions, sunscreen creams and lotions, after-sun creams and lotions, hand creams and lotions, foot creams and lotions, depilatory creams and lotions, after-shave creams and lotions, tanning creams and lotions, hair care products, for example hair sprays, hair gels, hair setting lotions, hair rinses, permanent and semi-permanent hair colorants, hair shaping agents such as cold waves and hair smoothing agents, hair tonics, hair creams and lotions, deodorants and antiperspirants, for example underarm sprays, roll-ons, deodorant sticks, deodorant creams, decorative cosmetic products, such as eye shadow, make-up, lipsticks, mascara, as well as candles, lamp oils, joss sticks, animal litter, cat litter, insecticides, repellents, liquid and gaseous fuels, heating oil and heating gases.

In a preferred embodiment, a preparation according to the invention or an article of daily use as described above contains one or more surface-active substances, preferably one or more surfactants and/or one or more emulsifiers. Surface-active substances allow the compounds of formula (1) to be used according to the invention to be incorporated more easily into the designated preparations or articles of daily use. Moreover, surface-active substances improve the release and effectiveness of the compounds of formula (1).

As already mentioned, the compounds of formula (1) to be used according to the invention are preferably used in cosmetic, body care, household and cleaning products. A preparation according to the invention is particularly preferred which is selected from the group consisting of cleaning agents, air fresheners, textile hygiene products, body care compositions, hair care products, deodorants, antiperspirants and animal litter. Such preparations or products are most preferably selected from the group consisting of:

cleaning agents, in particular floor cleaners, window cleaners, dishwashing detergents, bath and sanitary cleaners, soft scrub cleaners, solid and liquid WC cleaners, WC sticks, WC blocks (liquid or solid), pulverulent and foam carpet cleaners, liquid detergents, powder detergents, laundry pre-treatment agents, bleaching agents, soaking agents, stain removers, fabric softeners, laundry soaps, washing tablets, disinfectants, surface disinfectants;

air fresheners, preferably membrane-based, in liquid or gel-type form or applied to a solid carrier, or as aerosol or pump sprays;

textile hygiene products, preferably nappies, sanitary towels, panty liners, plasters, cleansing wipes;

body care compositions, preferably solid and liquid soaps, shower gels, shampoos, shaving soaps, shaving foams, bath oils, damp cleansing wipes, depilatory creams and lotions, tanning creams and lotions;

hair care products, preferably hair sprays, hair gels, hair setting lotions, hair rinses, permanent and semi-permanent hair colorants, hair creams and lotions;

deodorants and antiperspirants, preferably underarm sprays, roll-ons, deodorant sticks, deodorant creams;

animal litter, in particular cat litter.

The information provided further above applies accordingly to the proportion of compounds of formula (1) or corresponding mixtures to be used according to the invention in the described products.

A particularly preferred preparation according to the invention (as described above), in particular as in an embodiment stated above as being (particularly) preferred, is a cosmetic product or body care product. A product of this type is advantageously present in an application form selected from the group consisting of sticks, creams, gels, lotions, foams, roll-on preparations, powder sprays, aerosol or non-aerosol sprays.

A particularly preferred preparation according to the invention (as described above) is a deodorant or antiperspirant for application to the human (or animal) body and which preferably contains (depending on the desired mode of action) one or more of the following active ingredients:

(1) antimicrobially active substances which inhibit the development of the microorganisms responsible for sweat odour; for example Triclosan® (5-chloro-2-(2,4-dichlorophenoxy)phenol), triclocarban, chlorohexidine, chlorohexidinehydrochloride, chlorohexidinediacetate, chlorohexidinedigluconate, 2-phenoxyethanol, farnesol, glycerol esters and ethers such as glycerol monolaurate, glycerol monocaprinate, hexoxyglycerin, octoxyglycerin (=ethylhexylglycerin, 3-(2-ethylhexyloxy-1,2-propanediol) or Sensiva® SC 50 (produced by Schülke & Mayr), aliphatic 1,2-diols for example 1,2-decanediol (EP 1 269 983), araliphatic alcohol as described for example in EP 799 174, preferably 4-methyl-4-phenyl-2-pentanol (vetikol; WO 03/024907) or 2-methyl-4-phenyl-2-butanol (1,1-dimethyl-3-phenylpropanol, alpha,alpha-dimethylphenethylcarbinol), 1-menthyl methylether as described in WO 02/41861, 2-benzylheptan-1-ol (jasmol; 2-n-pentyl-3-phenylpropan-1-ol), 2,2-dimethyl-3-phenylpropanol (muguet alcohol; cf. U.S. Pat. No. 4,091,090), antimicrobially active secondary alcohols, as described for example in WO 2005/004601, in particular 3-methyl-6-phenyl-2-hexanol, 4-(2,4-dimethylphenyl)-2-butanol, 6-(4-isopropylphenyl)-3-methyl-2-hexanol, 4-(2,4,5-trimethylphenyl)-2-butanol, 3,3-dimethyl-4-phenyl-2-butanol, 3-methyl-4-(2-methylphenyl)-2-butanol, 6-(3,4-dimethylphenyl)-2-hexanol, aliphatic carboxylic acids such as 2-hexyloctanoic acid, 2-hexyldecanoic acid, 2-butyloctanoic acid or 2-butyldecanoic acid;

(2) enzyme-inhibiting substances which suppress the action of enzymes which play a part in the formation of sweat odour; for example citric acid esters and metal-chelating substances, such as EDTA (ethylenediamine tetra-acetic acid), EGTA (ethylenebis(oxyethylenenitrilo)-tetra-acetic acid] and DTPA (diethylenetriaminepenta-acetic acid, pentetic acid);

(3) odour-absorbing substances which absorb substances responsible for sweat odour; for example zinc ricinoleate, cyclodextrins;

(4) antiperspirants which inhibit the secretion of sweat and thus remove the bacteria responsible for the body odour from the breeding ground. Generally used as antiperspirants are preferably astringent metal salts, particularly inorganic and organic metal salts of the elements aluminium, zinc, magnesium, tin and zirconium as well as the mixtures thereof, halides such as aluminium chloride, basic aluminium hydroxychlorides, zirconyl oxychlorides and zirconyl hydroxychlorides as well as the mixtures thereof being used in particular. These aluminium and zirconium salts and the mixtures thereof are often also used in a complexed form, propylene glycol, polyethylene glycol or glycine preferably being used as complexing agent.

Preferably a preparation according to the invention (as described above), more preferably a preparation stated above as being (particularly) preferred is used to reduce an unpleasant odour or as an (auxiliary) mixture to reduce an unpleasant odour, in particular a human body odour, particularly human sweat odour, most particularly an armpit sweat odour.

In the present context, a method is relevant which can be used to assess whether a specific substance is suitable for a specific masking task, i.e. whether by using this substance an (unpleasant) odour can be reduced in the sense of the present invention.

A sample of an (odorous) substance or an (odorous) substance mixture which is to be tested for its capability in respect of neutralising or reducing an unpleasant odour is usually evaporated with an unpleasant smelling mixture in a defined air space and the resulting odour impression is determined in olfactory manner by a panel of testers. Accordingly, the development or the detection and checking of a substance or a corresponding substance mixture which neutralises or reduces an unpleasant odour is currently very expensive.

Therefore, according to our own experiments, a method is now used for testing the suitability of a test substance (optionally neutralising substance (N) to be tested) comprising a (i)(a) single alcohol of formula (1) and/or (i)(b) a mixture comprising or consisting of two or more different alcohols of formula (1) as defined further above, for checking the reduction of an unpleasant odour, comprising the following steps:
a) production or preparation of a malodorous standard mixture (unpleasant smelling standard mixture (S)) comprising or consisting of a substance having an unpleasant odour (malodorous substance (M)), i.e. a substance or a mixture,
b) production or preparation of a test mixture (T) likewise comprising the substance (M) and comprising the test substance (N), and
c) comparison of the malodorous impressions of malodorous standard mixture (S) and test mixture (T).

The test substance (N) and/or the test mixture (T) is advantageously a preparation according to the invention (as described further above). Furthermore, it is thus also preferred if the test substance (N) or test mixture (T) comprises one or more odorous substances in addition to the one or more alcohols of formula (1). The details provided further above applies accordingly to the number and selection of the odorous substances to be used. However, in the context of the method according to the invention, it is preferred if the test substance (N) does not itself contain any unpleasant smelling (odorous) substances.

The test method is preferably carried out at a temperature of 20° C. and under a pressure of 1013 mbar. Accordingly, a method as described above is particularly preferred, the comparison according to step c) being carried out at a temperature of 20° C. and under a pressure of 1013 mbar. If appropriate, steps a) or b) can also be carried out under the mentioned reaction conditions.

As already mentioned, the test substance (N) to be used according to the invention preferably also contains one or more odorous substances and more preferably optionally further auxiliaries or active ingredients (in particular those as described above). In this manner, more complex (odorous) substance mixtures such as, for example chords of odorous substances and ethereal oils or perfume oils can be tested for their suitability in respect of neutralising or reducing odours, in particular unpleasant odours. The information provided further above applies accordingly to the unpleasant odours used in the context of a method according to the invention.

A defined quantity of an unpleasant smelling mixture, i.e. a substance (M) is preferably used in the context of carrying out the described (test) method according to the invention. This means that the test method is preferably carried out such that the concentrations of substance (M) in the malodorous standard mixture (S) and in the test mixture (T) are the same. This permits a particularly good comparison of the two mixtures.

A method of this type is preferably carried out in that a respective test mixture (T) comprising a substance (M) and a test substance (N) are tested in vessels of the same size in respect of their suitability for reducing or neutralising an unpleasant odour (of the substance (M)) compared to other test mixtures and/or compared to the malodorous standard mixture (S).

The malodorous impressions of the malodorous standard mixture (S) and of the test mixture (T) and preferably also the perfume or fragrance intensity of these mixtures are preferably assessed against one another in each case by 8 or more testers (experts) who smell the resulting odours and fragrances. In the assessment, the malodorous standard mixture (S) is allocated an intensity of 6. The testers are selected as a function of their ability to assess in a reproducible manner the strength of odours. Before the test series, the testers are trained to recognise the unpleasant odours (to be reduced).

Further details and features of a method of this type according to the invention will emerge from the following Examples.

EXAMPLES

Unless stated otherwise, all amounts relate to weight.

The odour-neutralising or odour-reducing mixture "PI 24902" (cf. Table 1) used in the following in the context of the present invention is a substance consisting of the two materials 2-methylpropionic acid-3-hydroxy-2,2-dimethyl-1-(1-methylethyl)-propylester (compound of formula (1a)) and 2-methylpropionic acid-3-hydroxy-2,2,4-trimethylpentylester (compound of formula (1b)). Concerned here is a mixture to be used according to the invention consisting of the two mentioned substances of formula (1a) or (1b) for reducing an (unpleasant) odour or as an auxiliary for reducing an (unpleasant) odour.

TABLE 1

| Mixture "PI 24902" of the constituting isomers (1a) and (1b) | |
|---|---|
| Compound | % by weight |
| 2-methylpropionic acid-3-hydroxy-2,2-dimethyl-1-(1-methylethyl)-propylester of formula (1a) | 40.8 |
| 2-methylpropionic acid-3-hydroxy-2,2,4-trimethylpentylester of formula (1b) | 59.2 |

As already described earlier, the alcohols to be used according to the invention and thus also the previously mentioned mixture "PI 24902" have only a very slight inherent odour. Consequently, "PI 24902" can be used in any fragrance directions.

The respective odour or odour impression was assessed within the context of the present test method on an intensity scale from 1="odourless" to 9="very strong". The respective arithmetic averages from the individual assessments are stated in the Tables which follow later on.

Example 1

Example 1.1

Selection and Training of the Testers

A. Selection criterion 1: the testers must be able to distinguish the various bad odours from an odourless solvent (dipropylene glycol=DPG). In the context of the present text, a bad odour is an unpleasant odour in the sense of the previously given definition.

For test "A", several smell strips (thin cardboard strips of an odourless paper) are dipped into a mixture comprising one or more bad odours, i.e. comprising one or more substances which generate an unpleasant odour impression (in humans). In addition, several smell strips are dipped into DPG (odourless). Only those testers who are able to correctly discern the smell strips in a test "bad odour-bad odour-DPG and DPG-DPG-bad odour" take part in further tests. This checks whether the tester can even smell the bad odour at all. This was carried out with all bad odours mentioned in the scope of the present text.

The testers were not tested for their ability to perceive the neutralising substances. These are virtually odourless and can only be distinguished with difficulty from the solvents conventional in perfumery, such as DPG, Abalyn DE or triethyl citrate. Testers who find it completely impossible to detect these substances will not detect a reduction in odour.

B. Selection criterion 2: the testers must be able to distinguish different intensities or concentrations of bad odours or of the corresponding substances imparting these odour impressions. For this purpose, samples of different concentrations of the respective bad odours are introduced into a defined air space. These samples are different malodorous standard mixtures (S) which contain in each case a different concentration of a substance (M) with an unpleasant odour. Accordingly, these mixtures have intensities, differing in strength, of the respective bad odour and thus have differently intensive malodorous impressions. These samples are sorted by the testers according to intensity (odour strength). The smelling sequence of the concentrations must be recognised and assessed correctly by the testers. Testers who have passed both tests (A, B) can take part in the raw material tests described in the following.

Unless otherwise stated, the tests specified in the following were carried out in 500 ml wide-neck flasks made of brown glass. The bad odour models, i.e. the substances with an unpleasant odour were applied in each case to a different point of a filter paper or on a different filter paper than the substance to be tested (N) (for example mixture "PI 24902"). This ruled out a chemical interaction of the substances with one another in the present test method. In other words, a test mixture (T) to be used according to the invention preferably comprises a substance (M) having an unpleasant odour and a test substance (N) in a sample container (for example in a glass), but where (M) and (N) are preferably not in an intermixed condition, but are present next to one another (as described above). All the samples are assessed on a scale of 1="odourless" to 9="very strong". A sample (unperfumed and characterised as such) with only a bad odour (i.e. a malodorous standard mixture) serves in each case as a reference for the testers. In the context of the present text, an "unperfumed sample" is a mixture comprising a substance (M) having an unpleasant odour, but not an alcohol of formula (1) or a corresponding mixture to be used according to the invention. This sample is defined at a value which can be different depending on the type of bad odour, but is usually "6". All the samples are preferably offered in encoded manner. At least one of the encoded samples is usually empty (only filter paper) or provided with an unperfumed bad odour (reference; as described above). This provides a further check of the testers and of the results which are obtained.

Example 1.2

Sweat Odour Test

1 µl of an imitated sweat solution (substance (M)) having an unpleasant odour) consisting of various short, organic acids, aldehydes and an odourless solvent was applied to a filter paper. 1 µl each of different substances (N) to be tested was also applied in each case to such a filter paper and introduced together with the sweat sample, i.e. the imitated sweat solution, into the glass. Each sample was left to rest, sealed, for 15 h. 8-12 testers assessed the samples in respect of perfume/fragrance intensity and sweat intensity (malodorous impression). The averages of the individual assessments are stated.

TABLE 2

| | Sweat test | |
| --- | --- | --- |
| NAME | Perfume intensity | Sweat intensity |
| "PI 24902" | 2.3 | 3.3 |
| Abalyn DE | 1.0 | 5.9 |
| Triethylcitrate | 1.2 | 5.7 |
| 3-methyl-2-butenoic acid-3,7-dimethyl-6-octenylester | 3.4 | 4.2 |
| Sweat reference | 1 | 6 |

The mixture "PI 24902" to be used according to the invention reduces the (unpleasant) sweat odour by 45% with only slight perfume intensity, i.e. with slight or hardly detectable inherent odour.

Example 1.3

Toilet Odour Test

1 µl of a solution (substance (M) having an unpleasant odour), the odour of which imitated the odour of a just used toilet, consisting of skatole, short, organic acids, thionaphthol and an odourless solvent was applied in each case to a filter paper. 1 µl each of different substances (N) to be tested was also applied to filter paper and introduced together with the toilet odour sample into a glass. The samples were left to rest, sealed, for 15 h. 8-12 testers assessed the samples in respect of perfume/fragrance intensity and toilet odour intensity (malodorous impression). The averages of the individual assessments are stated.

Example 3

Toilet Odour Test

| NAME | Perfume intensity | Toilet odour intensity |
|---|---|---|
| "PI 24902" | 3.0 | 2.5 |
| Abalyn DE | 1.6 | 4.7 |
| Triethylcitrate | 1.0 | 5.8 |
| 3-methyl-2-butenoic acid-3,7-dimethyl-6-octenylester | 3.0 | 3.7 |
| Toilet odour reference | 1 | 6 |

The substance mixture "PI 24902" to be used according to the invention reduces the (unpleasant) toilet odour by 58%.

Example 1.4

Cooking Odour Test

1 µl of a solution (substance (M) having an unpleasant odour), the odour of which imitated the odour of a frequently used kitchen, consisting of fats, various frying aromas and an odourless solvent was applied in each case to a filter paper. 1 µl each of different substances (N) to be tested was also applied to filter paper and introduced together with the cooking odour sample into a glass. The samples were left to rest, sealed, for 15 h. 8-12 testers assessed the samples in respect of fragrance intensity and cooking odour intensity (malodorous impression). The averages of the individual assessments are stated.

TABLE 4

| cooking odour test | | |
|---|---|---|
| NAME | Perfume intensity | Cooking odour intensity |
| "PI 24902" | 2.3 | 4.3 |
| Abalyn DE | 1.1 | 5.8 |
| Triethylcitrate | 1.2 | 6.0 |
| Cooking odour reference | 1 | 6 |

The substance mixture "PI 24902" to be used according to the invention reduces the (unpleasant) cooking odour by 28%.

Example 1.5

Fish Odour Test

1 µl each of different substances (N) to be tested was applied to filter paper and introduced into a glass. The samples were left to rest, sealed, for 15 h. 400 µl in each case of a solution (substance (M) having an unpleasant odour), the odour of which imitated the odour of old fish, consisting of trimethylamine and an odourless solvent were pipetted onto a cotton wool pad and also introduced into the glass approximately 10 minutes before the assessment. 8-12 testers assessed the samples in respect of the fragrance intensity and fish odour intensity (malodorous impression). The averages of the individual assessments are stated.

TABLE 5

| Fish odour test | | |
|---|---|---|
| NAME | Perfume intensity | Fish odour intensity |
| "PI 24902" | 1.9 | 3.3 |
| Abalyn DE | 1.3 | 3.4 |
| Triethylcitrate | 1.1 | 5.5 |
| 3-methyl-2-butenoic acid-3,7-dimethyl-6-octenylester | 1.5 | 4.9 |
| Fish odour reference | 1 | 6 |

The substance mixture "PI 24902" to be used according to the invention reduces the fish odour by 45%.

Example 1.6

Smoke Odour Test

A plurality of cosmetic cotton wool pads was suspended from a frame. The frame was covered by a beaker. Half a cigarette was left under the overturned beaker ventilated from below, filling it with smoke. The cotton wool pads thus intensively absorbed the smoke odour. Each one of the cotton wool pads was placed in a beaker. 1 µl each of different substances (N) to be tested was applied to filter paper and introduced into the glass together with the smoke odour sample. The sample was left to rest, sealed, for 15 h. 8-12 testers assessed the samples in respect of the fragrance intensity and smoke odour intensity (malodorous impression). The averages of the individual assessments are stated.

TABLE 6

| Smoke odour test | | |
|---|---|---|
| Name | Perfume intensiy | Smoke odour intensity |
| "PI 24902" | 2.4 | 4.2 |
| Abalyn DE | 1.2 | 5.4 |
| Triethylcitrate | 1.2 | 5.8 |
| Smoke odour reference | 1 | 6 |

The substance mixture "PI 24902" to be used according to the invention reduces the (unpleasant) smoke odour by 30%.

Example 1.7

Butyric Acid Odour Test

1 µl each of different substances (N) to be tested was applied to filter paper and introduced into a glass. The samples were left to rest, sealed, for 15 h. 400 µl of a solution (substance (M) having an unpleasant odour), consisting of butyric acid and an odourless solvent were pipetted onto a cotton wool pad and also introduced into the glass approximately 10 minutes before the assessment. 8-12 testers assessed the samples in respect of the fragrance intensity and butyric acid odour intensity (malodorous impression). The averages of the individual assessments are stated.

TABLE 7

Butyric acid odour test

| NAME | Perfume intensity | Butyric acid odour intensity |
|---|---|---|
| "PI 24902" | 3.4 | 3.5 |
| Abalyn DE | 1.2 | 5.7 |
| Triethylcitrate | 1.1 | 5.5 |
| Butyric acid reference | 1 | 6 |

The substance mixture "PI 24902" to be used according to the invention reduces the (unpleasant) butyric acid odour by 42%.

Example 2

Use Combined with Odorous Substances (of Group (B))

The (odorous) materials or substances listed in the following Tables were mixed together in the stated ratios to produce corresponding mixtures (A1, A2; B1, B2).

TABLE 8

Mixture of "Lavendel" fragrance type

| NAME | A1 % by weight | A2 % by weight |
|---|---|---|
| FLORAZONE (4-ethyl-alpha,alpha-dimethyl-ethyl-phenylpropanal) | 3 | 3 |
| CYCLOGALBANAT ® ((cyclohexyloxy)-acetic acid-2-propenylester) | 1 | 1 |
| DIHYDROMYRCENOL (2,6-dimethyl-7-octen-2-ol) | 33 | 33 |
| EUCALYPTOL (1,3,3-trimethyl-2-oxabicyclo[2.2.2]octane) | 10 | 10 |
| TERPINENOL-4 (4-methyl-1-(1-methylethyl)-3-cyclohexen-1-ol) | 1 | 1 |
| ISOBORNYLACETATE (1,7,7-trimethyl-bicyclo[2.2.1]heptane-2-olacetate) | 3 | 3 |
| CANTRYL ® (2,2,3-trimethyl-3-cyclopentene-1-acetonitrile) | 6 | 6 |
| CYCLOHEXYLMAGNOL (alpha-methyl-cyclohexanepropanol) | 4 | 4 |
| COUMARONE (1-(2-benzofuranyl)-ethanone) | 4 | 4 |
| MADRANOL ® (alpha-ethyl-2,2,6-trimethyl-(Z)-cyclohexanepropanol) | 6 | 6 |
| TRIETHYLCITRATE | 29 | — |
| "PI 24902" | — | 29 |

TABLE 9

Mixture of "Citrus" fragrance type

| NAME | B1 % by weight | B2 % by weight |
|---|---|---|
| FARENAL ® (2,6,10-trimethyl-9-undecenal) | 4.1 | 4.1 |
| VERTACETAL ® COEUR (2,4,6-trimethyl-4-phenyl-1,3-dioxane) | 2.1 | 2.1 |
| CITROWANIL ® B (alpha-ethenyl-alpha-methyl-phenylpropanenitrile) | 2.1 | 2.1 |
| HYDROCITRONITRILE (beta-methyl-phenylpentanenitrile) | 5.4 | 5.4 |
| EUCALYPTOL (1,3,3-trimethyl-2-oxabicyclo[2.2.2]octane) | 0.6 | 0.6 |
| MANDARIL (3,12-tridecadienenitrile) | 1.3 | 1.3 |
| CANTRYL ® (2,2,3-trimethyl-3-cyclopentene-1-acetonitrile) | 1.1 | 1.1 |
| CYCLOANANATE (2-cyclopentene-1-actic acid-2-ethylbutylester) | 2.7 | 2.7 |
| PYROPRUNATE (2-butenoic acid-(1.1'-bicyclopentyl)-2-ylester) | 1.1 | 1.1 |
| CYCLOHEXYLMAGNOL (alpha-methyl-cyclohexanepropanol) | 31 | 31 |
| CHRYSANTHEME (2,2-dimethyl-1-(2,4-dimethyl-3-cyclohexen-1-yl)-1-propanone) | 7.5 | 7.5 |
| ROSAPHEN (beta-methyl-phenylpentanol) | 5.9 | 5.9 |
| BENZYLACETATE | 13.2 | 13.2 |
| PALISANDAL (1,1-dimethoxy-cyclododecane) | 4.5 | 4.5 |
| ISOMUSCONE (cyclohexadecanone) | 0.5 | 0.5 |
| TRIETHYLCITRATE | 16.9 | — |
| "PI 24902" | — | 16.9 |

The mixtures A1, A2, B1 and B2 were also tested in 500 ml wide-neck flasks made of brown glass. The bad odour models were applied in each case to a different point of a filter paper or on a different filter paper than the substance to be tested (as described above), to rule out a chemical interaction of the substances with one another. All the samples are assessed on a scale of 1="odourless" to 9="very strong". A sample (unperfumed and characterised as such) with only a bad odour (malodorous standard mixture (S)) serves in each case as a reference for the testers. This sample is defined at a value which can be different depending on the type of bad odour, but is usually "6". All the samples are preferably offered in encoded manner. At least one of the encoded samples is usually empty (only filter paper) or provided with an unperfumed bad odour (reference). Since complex perfume oils and mixtures usually have a stronger effect in respect of unpleasant odours compared to individual chemicals, the mixtures are preferably tested in a smaller quantity than the individual chemicals.

Example 2.1

Test of the Mixtures A1 to B2 (A1, A2, B1, B2) on Butyric Acid 0.5 µl each of the mixtures A1 to B2 were applied to filter paper and introduced into a glass. The sample was left to rest, sealed, for 15 h. 400 µl of a solution consisting of butyric acid and an odourless solvent (cf. Example 1.7) were pipetted onto a cotton wool pad and also introduced into the glass approximately 10 minutes before the assessment. 8-12 testers assessed the samples in respect of the fragrance intensity and butyric acid odour intensity (malodorous impression). The averages of the individual assessments are stated.

TABLE 10

Mixtures against butyric acid odour

| NAME | Perfume intensity | Butyric acid intensity |
|---|---|---|
| Mixture A1 | 4.9 | 2.9 |
| Mixture A2 | 5.8 | 1.8 |
| Mixture B1 | 4.7 | 2.9 |
| Mixture B2 | 5.1 | 1.9 |
| Butyric acid reference | 1 | 6 |

Surprisingly, the admixture of the perfume oils A2 and B2 according to the invention results in a particularly high reduction of the (unpleasant) butyric acid odour.

Example 2.2

Test of the Mixtures A1 to B2 on Sweat Odour

1 µl each of an imitated sweat solution (cf. Example 1.2) consisting of various short, organic acids, aldehydes and an odourless solvent was applied to a filter paper. 0.5 µl each of the mixtures A1 to B2 were also applied to filter papers and introduced together with the sweat sample into a glass. The samples was left to rest, sealed, for 15 h. 8-12 testers assessed the samples in respect of the fragrance intensity and sweat intensity (malodorous impression). The averages of the individual assessments are stated.

TABLE 11

Mixtures against sweat odour

| Name | Perfume intensity | Sweat odour intensity |
|---|---|---|
| Mixture A1 | 6.2 | 3.1 |
| Mixture A2 | 6.2 | 2.5 |
| Mixture B1 | 5.2 | 2.0 |
| Mixture B2 | 6.5 | 1.3 |
| Sweat odour reference | 1 | 6 |

Surprisingly, the addition of the perfume oils A2 and B2 results in a greater reduction of the (unpleasant) sweat odour compared to that of the perfume oils A1 and B1.

Example 2.3

Test of the Mixtures A1 to B2 on Smoke Odour

A plurality of cosmetic cotton wool pads was suspended from a frame. The frame was covered by a beaker. Half a cigarette was left under the overturned beaker ventilated from below, filling it with smoke. The cotton wool pads thus intensively absorbed the smoke odour (cf. Example 1.6). Each one of the cotton wool pads was placed in a beaker. 0.5 µl each of the mixtures A1 to B2 were applied to filter paper and introduced into the glass together with a smoke odour sample. The samples were left to rest, sealed, for 15 h. 8-12 testers assessed the samples in respect of the fragrance intensity and smoke odour intensity (malodorous impression). The averages of the individual assessments are stated.

TABLE 12

Mixtures against smoke odour

| NAME | Perfume intensity | Smoke odour intensity |
|---|---|---|
| Mixture A1 | 3.9 | 4.6 |
| Mixture A2 | 4.6 | 2.9 |
| Mixture B1 | 5.5 | 2.5 |
| Mixture B2 | 6.1 | 1.8 |
| Smoke odour reference | 1 | 7 |

Surprisingly, the admixture of the perfume oil A2 respectively B2 according to the invention results in a greater reduction of the (unpleasant) smoke odour compared to that of the perfume oil A1 respectively B1.

Example 3

Perfume Oil with Rose Smell Containing "PI 24902"

| Component/NAME | Parts by weight |
|---|---|
| Acetophenone, 10% in DPG | 10.00 |
| n-undecanal | 5.00 |
| Aldehyde C14 so-called (peach aldehyde) | 15.00 |
| Allylamylglycolate, 10% in DPG | 20.00 |
| Amylsalicylate | 25.00 |
| Benzylacetate | 60.00 |
| Citronellol | 80.00 |
| d-limonene | 50.00 |
| Decenol trans-9 | 15.00 |
| Dihydromyrcenol | 50.00 |
| Dimethylbenzylcarbinylacetate | 30.00 |
| Diphenyloxide | 5.00 |
| Eucalyptol | 10.00 |
| Geraniol | 40.00 |
| Nerol | 20.00 |
| Geranium oil | 15.00 |
| Hexenol cis-3, 10% in DPG | 5.00 |
| Hexenylsalicylate cis-3 | 20.00 |
| Indole, 10% in DPG | 10.00 |
| Alpha-ionone | 15.00 |
| Beta-ionon | 5.00 |
| Lilial (2-methyl-3-(4-tert-butyl-phenyl)propanal) | 60.00 |
| Linalool | 40.00 |
| Methylphenylacetate | 10.00 |
| Phenylethyl alcohol | 275.00 |
| Styrolylacetate | 20.00 |
| Terpineol | 30.00 |
| Tetrahydrolinalool | 50.00 |
| Cinnamyl alcohol | 10.00 |
| "PI 24902" | 200.00 |
| Total: | 1,200.00 |

Example 4

Perfume Oil with White Blossom Smell Containing "PI 24902"

| Component/NAME | Parts by weight |
|---|---|
| Benzylacetate | 60.00 |
| Citronellylacetate | 60.00 |
| Cyclamene aldehyde (2-methyl-3-(4-isopropylphenyl)propanal | 20.00 |
| Dipropylene glycol | 60.00 |
| Ethyllinalool | 40.00 |
| Florol (2-isobutyl-4-methyltetrahydro-2H-pyran-4-ol) | 30.00 |
| Globanone [(E/Z)-8-cyclohexadecen-1-one] | 180.00 |
| Hedione (methyldihydrojasmonate) | 140.00 |
| Hexenylsalicylate, cis-3 | 10.00 |
| Vertocitral (2,4-dimethyl-3-cyclohexenecarboxaldehyde) | 5.00 |
| Hydratropaaldehyde, 10% in DPG | 5.00 |
| Isodamascone (1-(2,4,4-trimethyl-2-cyclohexen-1-yl)-2-buten-1-one, 10% in DPG | 5.00 |
| Isomuscone (cyclohexadecanone) | 40.00 |
| Jacinthaflor (2-methyl-4-phenyl-1,3-dioxolane) | 10.00 |
| Cis-jasmone, 10% in DPG | 20.00 |
| Linalool | 50.00 |
| Linalylacetate | 30.00 |
| Methylbenzoate, 10% in DPG | 25.00 |
| para-methyl cresol, 10% in DPG | 10.00 |

| Component/NAME | Parts by weight |
| --- | --- |
| Nerol | 20.00 |
| Phenylpropylaldehyde | 5.00 |
| 2-Phenylethyl alcohol | 82.00 |
| Tetrahydrogeraniol | 13.00 |
| 2,2-dimethyl-3-cyclohexyl-1-propanol | 80.00 |
| "PI 24902" | 280.00 |
| Total: | 1,280.00 |

Example 5

Formulation and Application Examples in Finished Products

Example F1

Deodorant Formulation in the Form of a Roll-on Gel

| Component/NAME | % by weight |
| --- | --- |
| 1,3-butylene glycol | 2.00 |
| PEG-40-hydrogenated castor oil | 2.00 |
| Hydroxyethylcellulose | 0.50 |
| "PI 24902" | 0.20 |
| Perfume oil | 0.30 |
| Preservative phenoxyethanol | 0.30 |
| Water | ad 100.00 |

Example F2

Cream

| Component/NAME | % by weight |
| --- | --- |
| Paraffin oil | 10.00 |
| Ozokerite | 4.00 |
| Vaseline | 4.00 |
| Vegetable oil | 10.00 |
| Wool wax alcohol | 2.00 |
| Aluminium stearate | 0.40 |
| "PI 24902" | 0.40 |
| Perfume oil | 0.70 |
| 1,2-pentanediol | 2.00 |
| Water | ad 100.00 |

Example F3

O/W Lotion

| Component/NAME | % by weight |
| --- | --- |
| Paraffin oil | 5.00 |
| Isopropyl palmitate | 5.00 |
| Cetyl alcohol | 2.00 |
| Beeswax | 2.00 |
| Ceteareth-20 | 2.00 |
| PEG-20-glyceryl stearate | 1.50 |
| Glycerin | 3.00 |
| "PI 24902" | 0.30 |
| Perfume oil | 0.80 |
| Parabene | 0.30 |
| Water | ad 100.00 |

Example F4

Air Freshener in Gel Form

| Component/NAME | | % by weight | % by weight |
| --- | --- | --- | --- |
| Demineralised water | | Ad 100.00 | Ad 100.00 |
| Genugel ® X-6424 (1) | (carrageenan) | 2.00 | 2.00 |
| "PI 24902" | | 0.20 | 0.30 |
| Perfume oil A2 from Ex. 2 | | 0.60 | — |
| Perfume oil from Ex. 3 | | — | 0.80 |
| Arkopal ® N 100 (3) or Tergitol ® NP 10 (4) | (emulsifer) | 3.50 | 3.50 |
| Preventol ® D 7 (5) | (preservative) | 5.00 | 5.00 |

Example F5

Air Freshener in Gel Form 5 g of Accurel (porous homo-polypropylene powder with 75% porosity, produced by Akzo Noble Faser AG, Obernburg, Germany) are charged with 15 g of the perfume oil from Example 4 by mixing both constituents under vacuum. The resulting powder is then stirred with 4.5 g of water under normal pressure (Mix 1). In a separate vessel, 2.5 g of carrageenan, 0.3 g of chloracetamide and 0.5 g of calcium chloride dehydrate are dissolved in 62 g of water with heating at a maximum of 75° C. Mix 1 is introduced into this solution with stirring and is homogenised. The resulting, preferable still warm mixture is poured into the desired mould (balls, semispheres, pads, cylinders, cuboids, cubes, shells or the like). After cooling to approximately 20° C., air fresheners are obtained in gel form, the charging of which with perfume oil from Example 4 is approximately 20%, based on the total weight of the air freshener.

Example F6

Foot Cream

| Component/NAME | % by weight |
| --- | --- |
| Soluan 5 | 2.00 |
| Methyl salicylate | 2.00 |
| Caprylic/capric triglyceride | 10.00 |
| Stearic acid | 5.00 |
| Cetyl alcohol | 1.00 |
| Glycerin | 2.00 |
| Dimethicone | 1.00 |
| Carbopol 984 | 0.50 |
| Triethanol amine | 1.50 |
| "PI 24902" | 0.60 |
| Perfume oil | 0.90 |

-continued

| Component/NAME | % by weight |
|---|---|
| Preservatives | q.s. (lat.: quantum satis) |
| Water | ad 100.00 |

Example F7

Setting Lotion

| Component/NAME | % by weight |
|---|---|
| Polyvinylpyrrolidone/vinylacetate/vinylpropionate-copolymer | 5.00 |
| Ethanol | 45.00 |
| "PI 24902" | 0.50 |
| Perfume oil, preservatives | 1.50 |
| Water | ad 100.00 |

Example F8

Face Mask

| Component/NAME | % by weight |
|---|---|
| PEG-50 Lanolin | 0.50 |
| Glyceryl stearate | 2.00 |
| Sunflower seed oil | 3.00 |
| Bentonite | 8.00 |
| Kaolin | 35.00 |
| Zinc oxide | 5.00 |
| "PI 24902" | 0.30 |
| Perfume oil | 0.30 |
| Preservatives | q.s. |
| Water | ad 100.00 |

Example F9

Skin Oil

| Component/NAME | % by weight |
|---|---|
| Cetyl palmitate | 3.00 |
| $C_{12-15}$-Alkylbenzoate | 2.00 |
| Polyisobutene | 10.00 |
| Squalane | 2.00 |
| "PI 24902" | 0.15 |
| Perfume oil | 0.30 |
| Preservatives | q.s. |
| Paraffin oil | ad 100.00 |

Example F10

Ointment

| Component/NAME | % by weight |
|---|---|
| Vaseline | 36.00 |
| Ceresine | 10.00 |
| Zinc oxide | 4.00 |
| Vegetable oil | 20.00 |
| "PI 24902" | 0.07 |
| Perfume oil | 0.10 |
| Preservatives | q.s. |
| Paraffin oil | ad 100.00 |

Example F11

Wet Cleansing Wipes

Preparation of a Composition or Mixture for Neutralising Unpleasant Odours in Wet Cleansing Wipes:

The following components are mixed to form a composition or mixture: 30 parts by weight of dipropylene glycol, 25 parts by weight of "PI 24902", 15 parts by weight of isopropyl myristate, 15 parts by weight of triethyl citrate and 15 parts by weight of benzyl benzoate. Using an emulsifier, a 0.05% aqueous solution is produced from this composition and is used to treat wet cleansing wipes. The treated wet cleansing wipes have a significantly more neutral smell compared to untreated wipes. This means that the typical (unpleasant) odour of wet cardboard can no longer be detected.

Example F12

Aerosol Spray with Action Against Tobacco Smoke Odours on Textiles

The following components are mixed to form a composition or mixture: 20 parts by weight of dipropylene glycol, 25 parts by weight of "PI 24902", 15 parts by weight of isopropyl myristate, 15 parts by weight of triethyl citrate, 5 parts by weight of benzyl benzoate and 20 parts by weight of a perfume oil containing 48% by weight of odorous substances of group (B). A water-based aerosol spray containing 1% by weight of this composition is sprayed onto curtains to which a strong tobacco smoke odour clings. After being sprayed, the curtains have a significantly more neutral smell, the (unpleasant) tarry smoke odour can no longer be detected. Similar effects can be achieved when the odour-neutralising composition is sprayed onto textiles, such as items of clothing and furniture cushions.

Example F13

Aerosol Spray with Action Against Cooking Odours on Textiles

The following components are mixed to form a composition or mixture: 20 parts by weight of dipropylene glycol, 30 parts by weight of "PI 24902", 15 parts by weight of isopropyl myristate, 15 parts by weight of triethyl citrate, 10 parts by weight of benzyl benzoate and 10 parts by weight of a perfume oil containing 55% by weight of odorous substances of group (B). A water-based aerosol spray containing 1% by weight of this composition is sprayed onto curtains or items of clothing to which a strong odour of fried onions and hot frying fat clings. After being sprayed, the curtains have a significantly more neutral smell, the (unpleasant) fatty, onion odour can no longer be detected.

Example F14

Microcapsules with Action Against Urine Odour (e.g. in Nappies)

The following components are mixed to form a composition or mixture: 25 parts by weight of "PI 24902", 10 parts by weight of isomenthyl acetate, 20 parts by weight of isopropyl myristate, 30 parts by weight of triethyl citrate and 15 parts by weight of benzyl benzoate. This composition is brought into a microencapsulated form (average particle size: 78 micrometers) with starch sodium octenyl succinate (E 1450) and a sugar alcohol by means of spray drying, such that the charging of the microcapsules with the above mentioned composition is 50% by weight. The microcapsules are placed between two layers of paper bonded at the edges and incorporated into a paper nappy. On contact with moisture, the odour-neutralising composition is released and significantly reduces the urine odour which develops, compared to untreated nappies.

Example F15

Neutralisation of the Odour of Unperfumed Washing Powder

The following components are mixed to form a composition or mixture: 20 parts by weight of dipropylene glycol, 25 parts by weight of "PI 24902", 15 parts by weight of isopropyl myristate, 15 parts by weight of triethyl citrate, 5 parts by weight of benzyl benzoate and 20 parts by weight of a perfume oil containing 35% by weight of odorous substances of group (B). A 0.3% solution of this composition is sprayed onto unperfumed washing powder. After spraying, the odour (of the washing powder) has become significantly more neutral, the fatty rancid odour can no longer be detected.

Example F16

Neutralisation of WC Odour

Example F16.1

Artificial WC Odour

By combining the following components, an artificial WC odour was produced according to Example 13 stated in U.S. Pat. No. 4,719,105:

| Component/NAME | Parts by weight |
|---|---|
| Dipropylene glycol | 62.82 |
| Skatole | 0.91 |
| beta-thionaphthol | 0.91 |
| Mercaptoacetic acid | 21.18 |
| Capronoic acid | 6.00 |
| p-cresylphenylacetate | 2.18 |
| N-methylmorpholine | 6.00 |

Example F16.2

The following components are mixed to form a composition or mixture: 30 parts by weight of dipropylene glycol, 25 parts by weight of "PI 24902", 15 parts by weight of isopropyl myristate, 15 parts by weight of triethyl citrate and 15 parts by weight of benzyl benzoate. 1% by weight of this composition and 4% by weight of a perfume oil composition with a fresh conifer odour are incorporated into a WC stick. For comparison, 5% by weight of the pure perfume oil composition are incorporated into another WC stick. For testing, smelling chambers approximately 2.5 m$^3$ in size are charged with the WC odour according to Example F16.1. The WC sticks are suspended in the WC bowls located in the smelling chambers. After operating the flush, the quality of the air in the chamber was evaluated after 30 minutes by a panel of experts. The WC sticks containing the odour-neutralising composition resulted in a significantly more neutral odour impression, the odour profile of the perfume oil emerged more clearly and cleanly. Similar effects can be achieved with the odour-neutralising composition and perfume oils of a flowery or citrus fresh type.

Example F16.3

The following components are mixed to form a composition or mixture: 30 parts by weight of dipropylene glycol, 25 parts by weight of "PI 24902", 15 parts by weight of isopropyl myristate, 15 parts by weight of triethyl citrate and 15 parts by weight of benzyl benzoate. 2.5% by weight of this composition and 7.5% by weight of a perfume oil composition with a fresh citrus odour are incorporated into an air freshener of the stearate or carrageenan type. For comparison, 10% by weight of the pure perfume oil composition are incorporated into another air freshener. For testing, smelling chambers approximately 2.5 m$^3$ in size are charged with an artificial WC odour (according to Example F16.1). After the air fresheners were set up, the quality of the air in the chamber was evaluated after 30 minutes by a panel of experts. The air fresheners containing the odour-neutralising composition resulted in a significantly more neutral odour impression, the odour profile of the perfume oil is clearer and cleaner.

Example F17

Neutralisation of the Odour of an Unperfumed Fabric Softener

A fabric softener base, prepared from 70 parts by weight of demineralised water, 0.25 parts by weight of concentrated hydrochloric acid, 1 part by weight of calcium chloride dehydrate, 0.5 parts by weight of polysorbate 20 and 27 parts by weight of Varisoft 315 (Witco) was mixed with 1.25 parts by weight of a perfume oil (containing 44% by weight an odorous substances of group (B)). As a result of adding 0.15 parts by weight of "PI 24902", the odour of the finished product is substantially more neutral, overall the product smells cleaner and fresher.

Example F18

Neutralisation of Cat Urine (Odour)

1 part by weight of a mixture, consisting of 70 parts by weight of perfume oil containing 64% by weight of odorous substances of group (B), and 30% by weight of "PI 24902" are sprayed, with mixing, onto 3000 parts by weight of cat litter (bentonite). For comparison, the same perfume oil without "PI 24902" is applied in the same quantity. After the addition of cat urine, it was found that the cat litter which was only treated with perfume oil only reduced the unpleasant odour of cat urine to an insufficient extent, while the cat litter which also contained the "PI 24902" had a relatively neutral smell and thus greatly reduced the unpleasant odour by the strong odour of cat urine.

Example F19

Underarm Spray

The following components are mixed to form a composition or mixture: 30 parts by weight of dipropylene glycol, 25 parts by weight of "PI 24902", 15 parts by weight of isopropyl myristate, 15 parts by weight of triethyl citrate, 10 parts by weight of benzyl benzoate and 5 parts by weight of 1-menthyl acetate. A deodorant spray having a moisturising effect is prepared from 0.6 parts by weight of this combination, 40 parts by weight of 80% alcohol, 1 part by weight of perfume oil (containing 37% by weight of odorous substances of group (B)) and 55% by weight of propellant (propane-butane mixture). For comparison, a spray of the same composition is prepared which does not contain an odour-neutralising composition, but does contain 1.2 parts by weight of perfume oil. When sprayed in the underarm region, it is found that the spray with the odour-neutralising composition reduces unpleasant sweat odour in a substantially better manner and the fragrance of the perfume oil is more noticeable.

Example F20

Hair Conditioner with UV Protection

| Component | INCI Name | % by weight | % by weight |
|---|---|---|---|
| Renex PEG 6000 | PEG-150 | 2.50 | 2.50 |
| Hair Conditioner Base | Cetyl alcohol, behentrimonium chloride, Triticum Vulgare (Wheat) bran extract, linoleic acid | 3.00 | 3.00 |
| PCL-Solid | Stearyl heptanoate, stearyl caprylate | 0.50 | 0.50 |
| Dow Corning 5200 | Laurylmethicone copolyol | 0.50 | 0.50 |
| Natrosol 250 HR | Hydroxyethylcellulose | 0.50 | 0.50 |
| Benzophenone-4 | Benzophenone-4 | 1.00 | 0.50 |
| Neo Heliopan AP | Disodium phenyl dibenzimidazole tetrasulphonate | 1.00 | 0.80 |
| Amino methyl propanol | Amino methyl propanol | 2.00 | 1.20 |
| Nipagin M | Methylparaben | 0.30 | 0.30 |
| Dow Corning 949 cationic emulsion | Amodimethicone, cetrimonium chloride, trideceth-12 | 2.00 | 2.00 |
| Perfume oil from Ex. 3 | Perfume | 0.80 | — |
| Perfume oil B2 from Ex.. 2 | Perfume | — | 0.80 |
| Water | Water (Aqua) | Ad 100 | Ad 100 |

Example F21

Deodorant Sticks

| Component/NAME | A % by weight | B % by weight |
|---|---|---|
| Sodium stearate | 8.00 | 8.00 |
| PPG-3 Myristyl ether | 70.00 | 70.00 |
| 1,2-propylene glygol | 10.00 | 10.00 |
| 1,1-dimethyl-3-phenylpropanol | 0.20 | 0.25 |
| 2-butyloctanoic acid | — | 0.20 |
| Perfume oil from Ex. 4 | 0.55 | — |
| Perfume oil A2 from Ex. 2 | — | 0.65 |
| Water | Ad 100 | Ad 100 |

Example F22

Microemulsion Gels

| Component/NAME | % by weight | % by weight |
|---|---|---|
| Glycerin isostearate | 1.80 | 2.00 |
| Octoxyglycerin | 1.00 | 0.80 |
| Ceteareth-15 | 5.20 | 5.00 |
| PEG-150 Distearate | 1.00 | 1.00 |
| Aluminium chlorohydrate | 5.00 | 5.00 |
| Isotridecylisononanoate | 3.30 | 3.50 |
| Cyclomethicone | 6.60 | 6.40 |
| "PI 24902" | 0.15 | — |
| Perfume oil from Ex. 4 | 0.60 | — |
| Perfume oil B2 from Ex. 2 | — | 0.70 |
| Water | Ad 100 | Ad 100 |

Example F23

Antiperspirant Formulations

| Component/NAME | % by weight | % by weight |
|---|---|---|
| Reach AZP-908 SUF | 24.00 | 22.00 |
| Cyclomethicone (Pentamer) | Ad 100 | Ad 100 |
| Polydecene (Silkflo 364 NF) | 17.50 | 20.00 |
| Neo Helipan OS (ethylhexyl salicylate, Symrise) | 2.50 | 1.00 |
| L-Menthyl lactate (Frescolate ML, Symrise) | 0.25 | — |
| Polyethylene | 3.00 | 3.00 |
| Hydrogenated caster oil | 2.00 | 2.00 |
| Promyristyl PM-3 | 7.00 | 7.00 |
| PEG-8 Distearate | 3.00 | 3.00 |
| Silicon dioxide (Cab-O-Sil M-5) | 1.00 | 1.00 |
| Stearyl alcohol | 15.00 | 10.00 |
| Octyldodecanol | — | 8.00 |
| "PI 24902" | 0.20 | — |
| Perfume oil | 0.75 | — |
| Perfume oil A2 from Ex. 2 | — | 0.95 |

Example F24

Suspension Sticks

| Component/NAME | % by weight | % by weight | % by weight |
|---|---|---|---|
| Stearyl alcohol | 20.00 | 20.00 | 20.00 |
| Cyclomethicone | Ad 100 | Ad 100 | Ad 100 |
| PPG-14 Butylether | 2.00 | 2.00 | 2.00 |
| Hydrogenated caster oil | 1.00 | 1.00 | 1.00 |
| Talc | 2.00 | 2.00 | 2.00 |
| Aluminium chlorohydrate, powder | 20.00 | 20.00 | 20.00 |

-continued

| Component/NAME | % by weight | % by weight | % by weight |
|---|---|---|---|
| Triclosan ® (5-chloro-2-(2,4-dichlorophenoxy)phenol) | 0.30 | — | 0.30 |
| Ethylhexylglycerin (Octoxyglycerin) | 0.50 | 0.80 | 0.50 |
| 1,1-Dimethyl-3-phenylpropanol | 0.30 | 0.40 | 0.35 |
| Anis alcohol | — | — | 0.15 |
| "PI 24902" | 0.25 | — | — |
| Perfume oil containing 55% by weight of odorous substances of group (B) | 0.70 | — | — |
| Perfume oil B2 from Ex. 2 | — | 0.85 | — |
| Perfume oil A2 from Ex. 2 | — | — | 0.75 |

Example F25

Deodorant Sprays

| Component/NAME | % by weight | % by weight | % by weight |
|---|---|---|---|
| PEG-40-hydrogenated caster oil | 3.00 | 3.00 | 3.00 |
| Ethylhexylglycerin (Octoxyglycerin) | 0.80 | 0.80 | 0.80 |
| Ethanol | 40.00 | 40.00 | 40.00 |
| Citrate buffer | 0.50 | 0.50 | 0.50 |
| 1,2-Hexanediol/1,2-octanediol (1:1) | — | 0.25 | 0.35 |
| Phenoxyethanol | 0.25 | 0.35 | — |
| Triclosan ® (5-chloro-2-(2,4-dichlorophenoxy)phenol) | 0.25 | — | — |
| 2-Benzylheptan-1-ol (Jasmol) | — | 0.05 | 0.15 |
| "PI 24902" | 0.25 | 0.10 | — |
| Perfume oil containing 80% by weight of odorous substances of group (B) | 0.90 | — | — |
| Perfume oil from Ex. 3 | — | 0.75 | — |
| Perfume oil B2 from Ex. 2 | — | — | 0.80 |
| Water | Ad 100 | Ad 100 | Ad 100 |

Example F26

Wax Crayons

| Component/NAME | % by weight | % by weight |
|---|---|---|
| Hydrogenated caster oil | 5.00 | 5.00 |
| Beeswax | 6.00 | 6.00 |
| Alkylbenzoate having 12 to 15 C atoms | 17.00 | 17.00 |
| Ceresin | Ad 100 | Ad 100 |
| Neo Heliopan AV (ethylhexyl methoxycinnamate, Symrise) | 1.00 | 2.00 |
| Neo Heliopan 357 (butyl methoxydibenzoylmethane, Symrise) | 1.00 | — |
| 1,2-Hexanediol/1,2-octanediol (1:1) | — | 0.50 |
| Phenoxyethanol | 0.50 | — |
| 1,1-Dimethyl-3-phenylpropanol | 0.20 | — |
| 2-Methyl-5-phenylpentan-1-ol (rosaphen) | — | 0.30 |
| "PI 24902" | 0.20 | — |
| Perfume oil containing 52% by weight of odorous substances of group (B) | 0.60 | — |
| Perfume oil A2 from Ex. 2 | — | 0.70 |

Example F27

Deodorant Sticks

| Component/NAME | % by weight | % by weight |
|---|---|---|
| Sodium stearate | 7.00 | 8.00 |
| Sodium palmitate | 1.00 | — |
| 1,2-propylene glycol | Ad 100 | Ad 100 |
| 1,2-butylene glycol | 3.00 | — |
| 1,1-dimethyl-3-phenylpropanol | — | 0.25 |
| 2-butyloctanoic acid | — | 0.50 |
| 2-hexyldecanoic acid | 0.30 | — |
| Polyethylene glycol(25)cetearylether | 3.00 | 3.00 |
| Ethanol | 20.00 | 20.00 |
| Farnesol | — | 0.25 |
| Triclosan ® (5-chloro-2-(2,4-dichlorophenoxy)phenol) | 0.30 | — |
| Parabene (mixture of methyl-, ethyl-, propyl-, butyl-, isobutylparaben) | 0.30 | — |
| 1,2-hexanediol/1,2-octanediol (1:1) | — | 0.50 |
| 1,2-pentanediol | 1.50 | — |
| (−)-alpha-Bisabolol, nat. | 0.10 | — |
| "PI 24902" | 0.20 | — |
| Perfume oil containing 39% by weight of odorous substances of group (B) | 0.60 | — |
| Perfume oil B2 from Ex. 2 | — | 0.75 |

Example F28

Antiperspirant Sticks

| Component/NAME | % by weight | % by weight |
|---|---|---|
| Phenyl trimethicon (SilCare TM Silicone 15 M 50) | 13.50 | 13.50 |
| Cetearyl alcohol | Ad 100 | Ad 100 |
| Cetiol CC (dicaprylyl carbonate) | 13.50 | 13.50 |
| Stearic acid | 3.50 | 3.50 |
| PEG-40-hydrogenated caster oil (Emulsogen TM HCO 040) | 4.10 | 4.10 |
| PEG-8 distearate (Cithrol 4 DS) | 4.10 | 4.10 |
| Petrolatum | 6.90 | 6.90 |
| Aluminium chlorohydrate | 13.80 | 13.80 |
| Aluminium zirconium trichlorohydrex Gly | 20.00 | 19.50 |
| Neo Heliopan ® Hydro (phenylbenzimidazole sulphonic acid, Symrise) | 2.00 | — |
| 2,2-dimethyl-3-phenylpropanol (muguet alcohol) | — | 0.25 |
| Ethylhexylglycerin (octoxyglycerin) | — | 0.30 |
| "PI 24902" | 0.25 | — |
| Perfume oil containing 72% by weight of odorous substances of group (B) | 0.80 | — |
| Perfume oil A2 from Ex. 2 | — | 1.00 |

SPECIFIC EMBODIMENTS

Specific embodiment one comprises use (i)(a) of a single alcohol of formula (1) or (i)(b) of a mixture comprising or consisting of two or more different alcohols of formula (1),

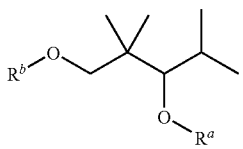

(1)

wherein in each case one of the two radicals $R^a$ or $R^b$ represents hydrogen and in each case the other radical $R^a$ or $R^b$ represents an acyl radical having 2 to 6 C atoms,
for reducing an odour
or
as an auxiliary for reducing an odour.

Specific embodiment two comprises use according to specific embodiment one, wherein the odour is an unpleasant odour.

Specific embodiment three comprises use according to either one of the preceding specific embodiments, wherein
in the alternative (i)(a) the acyl radical having 2 to 6 C atoms of the alcohol or
in the alternative (i)(b) the acyl radical having 2 to 6 C atoms of one, two, more or all of the alcohols
is selected from the group consisting of acety, propionyl, n-butyryl, isobutyryl, crotonyl, n-pentanoyl, isopentanoyl, n-hexanoyl and isohexanoyl, preferably selected from the group consisting of n-butyryl, isobutyryl and crotonyl.

Specific embodiment four comprises use according to any one of the preceding specific embodiments, of a mixture comprising or consisting of a first alcohol of formula (1) and a second alcohol of formula (1). wherein
the radical $R^a$ of the first alcohol has the meaning of $R^b$ of the second alcohol
and
the radical $R^b$ of the first alcohol has the meaning of $R^a$ of the second alcohol.

Specific embodiment five comprises use according to any one of specific embodiments one to three
(i)(a) of a single alcohol of formula (1a) or (1b), or
(i)(b) of a mixture comprising or consisting of an alcohol of formula (1a) and of an alcohol of formula (1b)

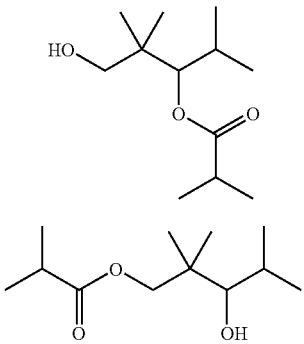

(1a)

(1b)

Specific embodiment five comprises use according to either specific embodiment four or specific embodiment five, wherein the weight ratio of the first alcohol of formula (1) to the second alcohol of formula (1) is within a range of from 10:1 to 1:10, preferably in a range of from 5:1 to 1:5.

Specific embodiment seven comprises use according to specific embodiment five, wherein the weight ratio of the two compounds (1a):(1b) is within a range of from 10:1 to 1:10, preferably in a range of from 5:1 to 1:5, more preferably in a range of from 2:1 to 1:3, most preferably in a range of from 3:2 to 1:2.

Specific embodiment eight comprises preparation consisting of or comprising
(i)(a) a single alcohol of formula (1) according to any one of specific embodiments one, two, three, or five, or
(i)(b) a mixture comprising or consisting of two or more different alcohols of formula (1), as defined in any one of specific embodiments one to seven, and
(ii) one or more, preferably two, three, four, five, six, seven, eight, nine, ten or more odorous substances, these odorous substances not being compounds of formula (1),
with the proviso that this preparation is not a preparation comprising 3-hydroxy-2,2,4-trimethylpentylisobutyrate and 2,2,4-trimethylpent-3-en-1-yl-isobutyrate.

Specific embodiment nine comprises preparation according to specific embodiment eight, wherein said preparation
(a) is a mixture for reducing an odour, or
(b) is a mixture in which during use individual constituents develop an unpleasant odour which is reduced by the presence of alcohol(s) of formula (1), or
(c) is a mixture in which one, two or more of the odorous substances of group (ii) have an unpleasant odour which is reduced by the presence of alcohol(s) of formula (1).

Specific embodiment ten comprises preparation according to either specific embodiment eight or specific embodiment nine, wherein the ratio of the total quantity of compounds of formula (1) to the total quantity of odorous substances, based on weight, is in a range of from 10:1 to 1:50, preferably in a range of from 5:1 to 1:30, more preferably in a range of from 2:1 to 1:20, most preferably in a range of from 3:2 to 1:10.

Specific embodiment eleven comprises preparation according to any one of specific embodiments eight to ten, wherein the one, two, more or all the odorous substances are selected from the group (B'), consisting of:
alpha-hexylcinnamic aldehyde, 2-phenoxyethylisobutyrate, dihydromyrcenol, methyldihydrojasmonate, 4,6,6,7,8,8-hexamethyl-1,3,4,6,7,8-hexahydrocyclopenta[g]benzopyrane, tetrahydrolinalool, benzylacetate, 2-methyl-3-(4-tert-butylphenyl)propanal, cinnamon alcohol, 1-phenylethylacetate, octahydro-2,3,8,8-tetramethyl-2-acetonaphthone, 2-acetyl-1,2,3,4,6,7,8-octahydro-2,3,8,8-tetramethylnaphthaline, 4-tert.-butylcyclohexylacetate, 2-tert.-butylcyclohexylacetate, alpha-ionone, terpinylacetate, 4-(4-hydroxy-4-methylpentyl)-3-cyclohexenecarboxaldehyde, alpha-amyl cinnamic aldehyde, 15-pentadec-11-enolide, 15-pentadec-12-enolide, 15-cyclopentadecanolide, cyclohexadecanone, 1-(5,6,7,8-tetrahydro-3,5,5,6,8,8-hexamethyl-2-naphthalenyl)ethanone, 2-ethyl-4-(2,2,3-trimethyl-3-cyclopenten-1-yl)-2-buten-1-ol, menthol, eucalyptol, anethol, geraniol, nerol, citronellol, linalylacetat, 2,2-dimethyl-3-(3-methylphenyl)-propanol, rose oxide, allylheptanoate, 4-methylacetophenone, timberol, benzylacetone, methylcinnamate, 3a,6,6,9a-tetramethyldodecahydronaphtho[2,1-b]furan, 2-methyl-5-phenylpentan-1-ol, 2-phenylethanol, linalool.

Specific embodiment twelve comprises preparation according to any one of specific embodiments eight to eleven, wherein the preparation also comprises (iii) one, two, three or more production auxiliaries, selected from the group (H) consisting of: dipropylene glycol (DPG), diethylphthalate (DEP), triethyl citrate (TEC), isopropylmyristate (IPM) and benzyl benzoate (BB).

Specific embodiment thirteen comprises preparation according to any one of specific embodiments eleven to twelve, comprising (a) one or more odorous substances of group (B') and one or more production auxiliaries of group (H)
or
(b) two or more odorous substances of group (B') and/or two or more production auxiliaries of group (H).

Specific embodiment fourteen comprises preparation according to any one of specific embodiments eight to thirteen, wherein the preparation is selected from the group consisting of cosmetic, body care, household and cleaning products.

Specific embodiment fifteen comprises preparation according to any one of specific embodiments eight to fourteen, wherein the preparation is selected from the group consisting of cleaning agents, air fresheners, textile hygiene products, body care compositions, hair care products, deodorants, antiperspirants and animal litter.

It is claimed:

1. A preparation comprising:
   (i) an odor reducing amount of a mixture of two different alcohols of formula (1)

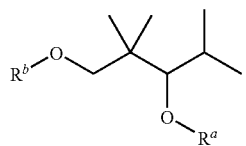

(1)

wherein on of $R^a$ and $R^b$ represents hydrogen and the other represents an acyl radical having 2 to 6 carbon atoms; and (ii) one of the following combinations of components selected from the group consisting of A and B:
(a) 4-ethyl-alpha, alpha-dimethyl-ethyl-phenylpropanal;
   (cyclo hexyloxy)-acetic acid-2-propenylester;
   2,6-dimethyl-7-octen-2-ol;
   1,3,3-trimethyl-2-oxabicyclo[2.2.2]octane;
   4-methyl-1-(1-methylethyl)-3-cyclohexen-1-ol;
   1,7,7-trimethyl-bicyclo[2.2.1]heptane-2-ol acetate;
   2,2,3-trimethyl-3-cyclopentene-1-acetonitrile;
   alpha-methyl-cyclohexanepropanol;
   1-(2-benzofuranyl)-ethanone; and
   alpha-ethyl-2,2,6-trimethyl-(Z)-cyclohexanepropanol; and
(b) 2,6,10-trimethyl-9-undecenal:
   2,4,6-trimethyl-4-phenyl-1,3-dioxane;
   alpha-ethenyl-alpha-methyl-phenylpropanenitrile;
   beta-methyl-phenylpentanenitrile;
   1,3,3-trimethyl-2-oxabicyclo[2.2.2]octane;
   3,12-tridecadienenitrile;
   2,2,3-trimethyl-3-cyclopentene-1-acetonitrile;
   2-cyclopentene-1-acetic acid-2-ethylbutylester;
   2-butenoic acid-(1,1'-bicyclopentyl)-2-yl ester;
   alpha-methyl-cyclohexanepropanol;
   2,2-dimethyl-1-(2,4-dimethyl-3-cyclohexen-1-yl)-1-propanone;
   beta-methyl-phenylpentanol;
   benzylacetate;
   1,1-dimethoxy-cyclododecane; and
   cyclohexadecanone.

2. The preparation according to claim 1, wherein the acyl radical having 2 to 6 carbon atoms is selected from the group consisting of acetyl, propionyl, n-butyryl, isobutyryl, crotonyl, n-pentanoyl, isopentanoyl, n-hexanoyl and isohexanoyl.

3. The preparation according to claim 1, wherein the acyl radical having 2 to 6 carbon atoms is selected from the group consisting of n-butyryl, isobutyryl and crotonyl.

4. The preparation according to claim 1, wherein $R^a$ of one alcohol of formula (1) is identical to $R^b$ of the other alcohol of formula (1).

5. The preparation according to claim 1, wherein the weight ratio of the first alcohol of formula (1) to the second alcohol of formula (1) is from 10:1 to 1:10.

6. The preparation according to claim 1, wherein the weight ratio of the first alcohol of formula (1) to the second alcohol of formula (1) is from 5:1 to 1:5.

7. The preparation according to claim 1, wherein one alcohol of formula (1) is an alcohol of formula (1a) and the other alcohol of formula (1) is an alcohol of formula (1b)

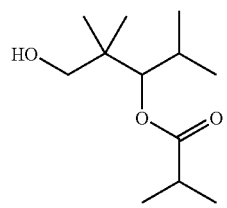

(1a)

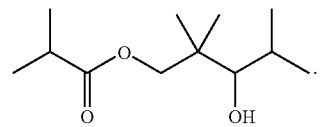

(1b)

8. The preparation according to claim 1, further comprising:
   (iii) one or more production auxiliaries selected from the group consisting of dipropylene glycol (DPG), diethylphthalate (DEP), triethyl citrate (TEC), isopropylmyristate (IPM), and benzyl benzoate (BB).

9. The preparation according to claim 1, wherein the preparation is selected from the group consisting of cosmetic, body care, household and cleaning products.

10. The preparation according to claim 1, where the preparation is selected from the group consisting of cleaning agents, air fresheners, textile hygiene products, body care compositions, hair care products, deodorants, antiperspirants, and animal litter.

* * * * *